(12) United States Patent
Venturino et al.

(10) Patent No.: US 6,981,297 B2
(45) Date of Patent: Jan. 3, 2006

(54) CONTROLLED PLACEMENT OF A REINFORCING WEB WITHIN A FIBROUS ABSORBENT

(75) Inventors: Michael B. Venturino, Appleton, WI (US); Steven P. Jones, Neenah, WI (US); Shannon K. Melius, Appleton, WI (US); Paul E. Olmstead, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 388 days.

(21) Appl. No.: 10/306,186

(22) Filed: Nov. 27, 2002

(65) Prior Publication Data

US 2004/0098838 A1 May 27, 2004

(51) Int. Cl.
*D01G 25/00* (2006.01)

(52) U.S. Cl. ............................................ 19/296; 19/301
(58) Field of Classification Search ................. 19/148, 19/296, 301, 302, 304, 307, 308; 29/895.2, 29/895.3; 198/397.03; 209/284, 288, 296, 209/297, 405, 406, 397, 399, 684, 686; 264/112, 264/121, 517, 518; 403/292, 294, 401; 425/80.1, 425/81.1, 83.1
See application file for complete search history.

(56) References Cited

U.S. PATENT DOCUMENTS

| | | |
|---|---|---|
| 3,085,309 A | 4/1963 | Olson |
| 3,156,751 A | 11/1964 | Valdes et al. |
| 3,587,579 A | 6/1971 | Sabee |
| 3,683,921 A | 8/1972 | Brooks et al. |

(Continued)

FOREIGN PATENT DOCUMENTS

| | | |
|---|---|---|
| DE | 198 23 954 A1 | 12/1999 |
| EP | 0 151 018 A2 | 8/1985 |
| EP | 0 226 939 A2 | 12/1986 |
| EP | 0 298 348 A1 | 11/1989 |
| EP | 0 399 511 A2 | 11/1990 |
| EP | 0 467 409 A1 | 1/1992 |
| EP | 0 297 180 B1 | 3/1992 |

(Continued)

OTHER PUBLICATIONS

International Search Report for PCT/US 03/00293 dated Jul. 29, 2003.
International Search Report, dated May 28, 2003 in PCT/US 03/00881, 8 pages.
International Search Report for PCT/US 03/01337 dated Jul. 21, 2003.
International Search Report for PCT/US03/15959 dated Feb. 3, 2004.
International Search Report for PCT/US03/16480 dated Oct. 13, 2003.

*Primary Examiner*—Gary L. Welch
(74) *Attorney, Agent, or Firm*—Senniger Powers

(57) ABSTRACT

Apparatus for forming an air formed, reinforced fibrous web has a form member on which fluent fibrous material is deposited in an air formed deposition process. The fibrous web may be used as an absorbent core of an absorbent article. The form member has a forming surface which is shaped and arranged to contact and support a reinforcing member, such as a web of scrim. The forming surface is particularly formed to locate the reinforcing member at the proper position within the thickness of the fibrous web. No additional locating structure is needed and the reinforcing member can be placed on the forming surface prior to entry into the forming chamber where fibrous material is deposited onto the forming chamber. A form and a method for making a reinforced fibrous web are also disclosed.

71 Claims, 20 Drawing Sheets

U.S. PATENT DOCUMENTS

| | | | |
|---|---|---|---|
| 3,816,231 A | | 6/1974 | Marshall |
| 3,856,012 A | | 12/1974 | MacDonald et al. |
| 3,862,877 A | | 1/1975 | Camden |
| 3,867,935 A | | 2/1975 | Eisdorfer et al. |
| 3,888,248 A | | 6/1975 | Moore et al. |
| 3,935,979 A | | 2/1976 | Hickey |
| 4,001,472 A | | 1/1977 | Thomas et al. |
| 4,028,455 A | * | 6/1977 | Ueda et al. ............ 425/388 |
| 4,141,772 A | | 2/1979 | Buell |
| 4,217,078 A | | 8/1980 | Buell |
| 4,235,237 A | | 11/1980 | Mesek et al. |
| 4,303,189 A | | 12/1981 | Wiley et al. |
| 4,392,862 A | | 7/1983 | Marsan et al. |
| 4,425,127 A | | 1/1984 | Suzuki et al. |
| 4,666,647 A | | 5/1987 | Enloe et al. |
| 4,674,966 A | | 6/1987 | Johnson et al. |
| 4,704,112 A | | 11/1987 | Suzuki et al. |
| 4,710,185 A | | 12/1987 | Sneyd, Jr. et al. |
| 4,761,258 A | | 8/1988 | Enloe |
| 4,764,325 A | | 8/1988 | Angstadt |
| 4,765,780 A | | 8/1988 | Angstadt |
| 4,773,903 A | | 9/1988 | Weisman et al. |
| 4,775,579 A | | 10/1988 | Hagy et al. |
| 4,810,568 A | | 3/1989 | Buyofsky et al. |
| 4,837,715 A | | 6/1989 | Ungpiyakul et al. |
| 4,904,440 A | | 2/1990 | Angstadt |
| 4,908,175 A | | 3/1990 | Angstadt |
| 4,915,897 A | * | 4/1990 | Farrington et al. ......... 264/517 |
| 4,927,346 A | | 5/1990 | Kaiser et al. |
| 4,927,582 A | | 5/1990 | Bryson |
| 5,004,579 A | | 4/1991 | Wislinski et al. |
| 5,017,324 A | | 5/1991 | Kaiser et al. |
| 5,124,188 A | | 6/1992 | Roe et al. |
| 5,128,082 A | | 7/1992 | Makoui |
| 5,139,841 A | | 8/1992 | Makoui et al. |
| 5,144,729 A | | 9/1992 | Austin et al. |
| 5,161,283 A | | 11/1992 | Hansen |
| 5,219,633 A | | 6/1993 | Sabee |
| 5,281,208 A | | 1/1994 | Thompson et al. |
| 5,302,445 A | | 4/1994 | DePetris et al. |
| 5,328,072 A | | 7/1994 | Ruessmann et al. |
| 5,389,095 A | | 2/1995 | Suzuki et al. |
| 5,389,202 A | | 2/1995 | Everhart et al. |
| 5,429,788 A | | 7/1995 | Ribble et al. |
| 5,447,677 A | | 9/1995 | Griffoul et al. |
| 5,466,409 A | | 11/1995 | Partridge et al. |
| 5,486,167 A | | 1/1996 | Dragoo et al. |
| 5,505,720 A | | 4/1996 | Walters et al. |
| 5,527,300 A | | 6/1996 | Sauer |
| 5,531,729 A | | 7/1996 | Coles et al. |
| 5,591,148 A | | 1/1997 | McFall et al. |
| 5,607,415 A | | 3/1997 | Datta et al. |
| 5,614,283 A | | 3/1997 | Potnis et al. |
| 5,672,306 A | | 9/1997 | Sprang et al. |
| 5,704,931 A | | 1/1998 | Holtman et al. |
| 5,756,039 A | | 5/1998 | McFall et al. |
| 5,762,844 A | | 6/1998 | Van Himbergen et al. |
| 5,772,813 A | | 6/1998 | Bitowft et al. |
| 5,803,334 A | | 9/1998 | Patel et al. |
| 5,818,719 A | | 10/1998 | Brandon et al. |
| 5,866,173 A | | 2/1999 | Reiter et al. |
| 5,871,613 A | | 2/1999 | Bost et al. |
| 5,873,963 A | | 2/1999 | Trombetta et al. |
| 5,902,757 A | | 5/1999 | Stern et al. |
| 5,916,661 A | | 6/1999 | Benson et al. |
| 5,925,439 A | | 7/1999 | Haubach |
| 5,938,648 A | | 8/1999 | LaVon et al. |
| 5,944,706 A | | 8/1999 | Palumbo et al. |
| 5,947,945 A | | 9/1999 | Cree et al. |
| 5,961,509 A | | 10/1999 | Kling |
| 5,997,520 A | | 12/1999 | Ahr et al. |
| 6,048,489 A | | 4/2000 | Reiter et al. |
| 6,060,637 A | | 5/2000 | Bitowft et al. |
| 6,107,538 A | | 8/2000 | Young et al. |
| 6,203,654 B1 | | 3/2001 | McFall et al. |
| 6,220,999 B1 | | 4/2001 | Kugler et al. |
| 6,258,996 B1 | | 7/2001 | Goldman |
| 6,262,331 B1 | | 7/2001 | Nakahata et al. |
| 6,284,943 B1 | | 9/2001 | Osborn, III et al. |
| 6,296,862 B1 | | 10/2001 | Paul et al. |
| 6,330,735 B1 | | 12/2001 | Hahn et al. |
| 6,375,644 B2 | | 4/2002 | Mizutani |
| 6,416,697 B1 | | 7/2002 | Venturino et al. |
| 6,492,574 B1 | | 12/2002 | Chen et al. |
| 6,533,978 B1 | | 3/2003 | Wisneski et al. |
| 6,533,989 B1 | | 3/2003 | Wisneski et al. |
| 6,630,096 B2 | * | 10/2003 | Venturino et al. .......... 264/518 |
| 2001/0039405 A1 | | 11/2001 | Keuhn, Jr. et al. |
| 2003/0116888 A1 | | 6/2003 | Rymer et al. |
| 2003/0119401 A1 | | 6/2003 | Chakravarty et al. |
| 2003/0132556 A1 | | 7/2003 | Venturio et al. |
| 2003/0139721 A1 | | 7/2003 | Melius et al. |
| 2004/0102752 A1 | | 5/2004 | Chen et al. |

FOREIGN PATENT DOCUMENTS

| | | |
|---|---|---|
| GB | 2168612 A | 6/1986 |
| JP | 09122172 | 5/1997 |
| JP | 10211236 | 8/1998 |
| WO | WO 93/18729 A1 | 9/1993 |
| WO | WO 96/00550 A1 | 1/1996 |
| WO | WO 99/22685 A1 | 5/1999 |
| WO | WO 99/25281 A1 | 5/1999 |
| WO | WO 00/10498 A1 | 3/2000 |
| WO | WO 00/37725 A1 | 6/2000 |
| WO | WO 00/63479 A1 | 10/2000 |
| WO | WO 01/92003 A1 | 12/2001 |
| WO | WO 03/059232 A2 | 7/2003 |

* cited by examiner

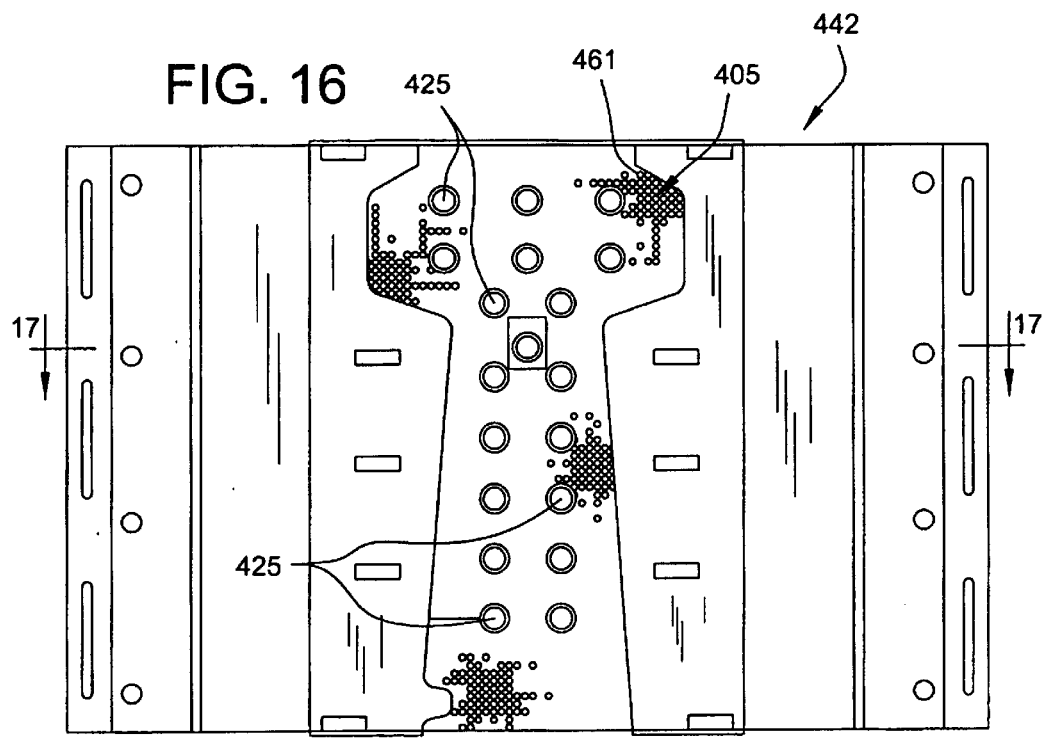
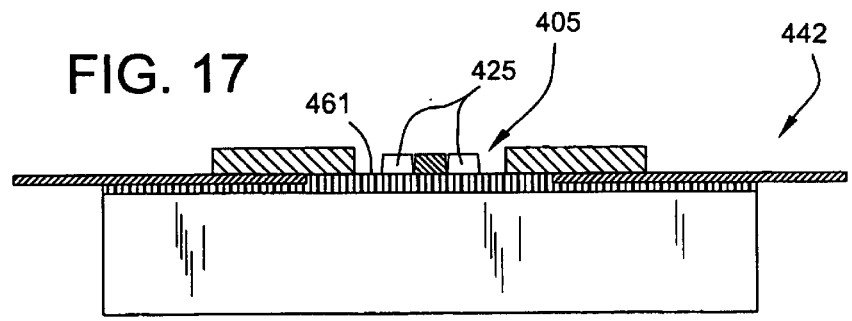

CONTROLLED PLACEMENT OF A REINFORCING WEB WITHIN A FIBROUS ABSORBENT

BACKGROUND OF THE INVENTION

This invention relates generally to apparatus, a form and a method for making an air formed, reinforced fibrous web and to a reinforced absorbent formed by such a web. The absorbent can be used for applications such as disposable diapers, child's training pants, feminine care articles, incontinence articles, bandages and the like.

Absorbent structures, such as for disposable absorbent garments, may include absorbent cores conventionally formed by air forming or air laying techniques. For example, the manufacture of the absorbent core may begin by fiberizing a fibrous sheet of cellulosic or other suitable absorbent material in a conventional fiberizer, or other shredding or comminuting device, to form discrete fibers. In addition, particles of superabsorbent material are mixed with the discrete fibers. The fibers and superabsorbent particles are then entrained in an air stream and directed to a foraminous forming surface upon which the fibers and superabsorbent particles are deposited to form an absorbent fibrous web. In addition, bonding agents or other strengthening components may be incorporated to provide a more stabilized web.

Other techniques are also employed to form webs of stabilized absorbent material. Such techniques have included dry-forming techniques, wet-laying techniques, foam-forming techniques, and various wet-forming techniques. The resulting webs of absorbent material have included absorbent fibers, natural fibers, synthetic fibers, superabsorbent materials, binders, and strengthening components in desired combinations. However formed, the absorbent web may then be stored or immediately directed for further processing (e.g., being cut into individual absorbent cores) and assembly with other components to produce a final absorbent article.

Absorbent materials have also been strengthened by adding reinforcing members on at least one side of the absorbent structure. Such reinforcement materials have included reinforcement filaments, tissue layers, fabric layers and netting materials. It is also known to add staple binder fibers to the absorbent materials upon formation of the absorbent core. The binder fibers are activated by heat to produce adhesion of the absorbent materials. Integrity of the absorbent core is desirable to avoid bunching, clumping, cracking and separating of the absorbent core in either a wet or a dry state. This improves the fit and comfort to the wearer even after the article receives insults. Sagging and drooping of the absorbent article can cause gaps between the article and the wearer's body which may lead to leaking. As absorbent cores are made both thinner and narrower (particularly in the crotch region), stresses encountered in manufacture and use can be high, requiring reinforcement. In manufacture, tension on the absorbent core can be particularly high during start up and shut down of processing machinery. In use, the lack of integrity can make the absorbent article fit poorly and impact product performance by breaking up the absorbent core, and thereby inhibiting fluid control, liquid handling and wicking which can contribute to leaking.

Co-assigned European Patent Publication No. 0 467 409 A1 discloses one attempt to reinforce an absorbent pad using a scrim material. In that disclosure, a netting or scrim material is used in which some strands have an inner core of one material and an outer sheath of a second material. The scrim is introduced into a forming chamber in which it is incorporated into a fibrous matrix. The second material of the sheath has a lower melting point than the first material of the core. After incorporation of the scrim into the fibrous matrix, the absorbent web formed is heated to melt the sheath for bonding the scrim to the fibers in the matrix. This requires an extra step in the manufacture of a reinforced absorbent.

European Publication No. 0 467 409 also discloses a method for establishing the position of the scrim within the fibrous matrix. Essentially, the location at which the scrim is introduced into the forming chamber is changed to change the depth at which the scrim will be located in the fibrous matrix. The later the scrim is introduced to the forming chamber, the nearer to the top or radially outer surface of the fibrous matrix on the forming drum the scrim will be located. The earlier the scrim is introduced into the forming chamber, the nearer to the bottom or radially inner surface of the fibrous matrix the scrim will be located. However, it is difficult to control placement of the scrim within a fibrous matrix, not only as to its depth within the matrix, but also its lateral position. The high rate flow of air within the forming chamber makes it difficult to maintain control of the scrim. Failure to properly position the scrim within the fibrous matrix can compromise its ability to reinforce an absorbent produced from the fibrous matrix and/or cause the scrim to become entangled in a scarfing roll or other absorbent forming device used to shape the web. If the scrim is laid directly on the forming surface of an air forming machine, it would reinforce the absorbent web only weakly. However, if the web is positioned near the top of the fibrous web, it will become entangled with the scarfing roll of the machine, causing the machine to stop operating until the entanglement is cleared. It will be appreciated that accuracy and consistency in the position of the scrim within the thickness of the absorbent web is desirable.

SUMMARY OF THE INVENTION

In one aspect of the present invention, a form for use in making an air formed, reinforced fibrous web generally comprises a foraminous surface having a length and a width and adapted to collect fluent fibrous material driven by fluid pressure toward the foraminous surface to form the fibrous web. The foraminous surface is formed to contact and support a reinforcing member at a location selected for positioning the reinforcing member within the thickness of the fibrous web.

In another aspect of the present invention, apparatus for forming a reinforced fibrous web generally comprises a form, a reinforcing member delivery system for delivering a reinforcing member to the form, a forming chamber adapted to deliver fluent fibrous material generally to the form, and a vacuum source for applying a vacuum to draw the fluent material onto the form. The form has a construction as set forth in the preceding paragraph.

In a further aspect of the present invention, a method for forming a reinforced fibrous web for use in the manufacture of absorbent articles includes moving a forming surface through a forming chamber. A reinforcing member is delivered into contact with the moving forming surface so that the reinforcing member is positioned relative to the forming surface by contact therewith. Fibrous material is delivered to the forming surface. In the forming chamber, at least some of the fibrous material passes through the reinforcing member on the forming surface and is deposited on the forming surface, and at least some of the fibrous material is entangled with the reinforcing member to form the fibrous web.

Other objects and features of the present invention will be in part apparent and in part pointed out hereinafter.

BRIEF DESCRIPTION OF THE DRAWINGS

FIG. 16 is a top plan view of one of the form members of FIG. 14;

FIG. 17 is a section taken in the plane including line 17—17 of FIG. 16 and illustrating placement of reinforcing scrim on the form member;

Corresponding reference characters indicated corresponding parts throughout the several views of the drawings.

DETAILED DESCRIPTION OF THE DRAWINGS

Figure 1:
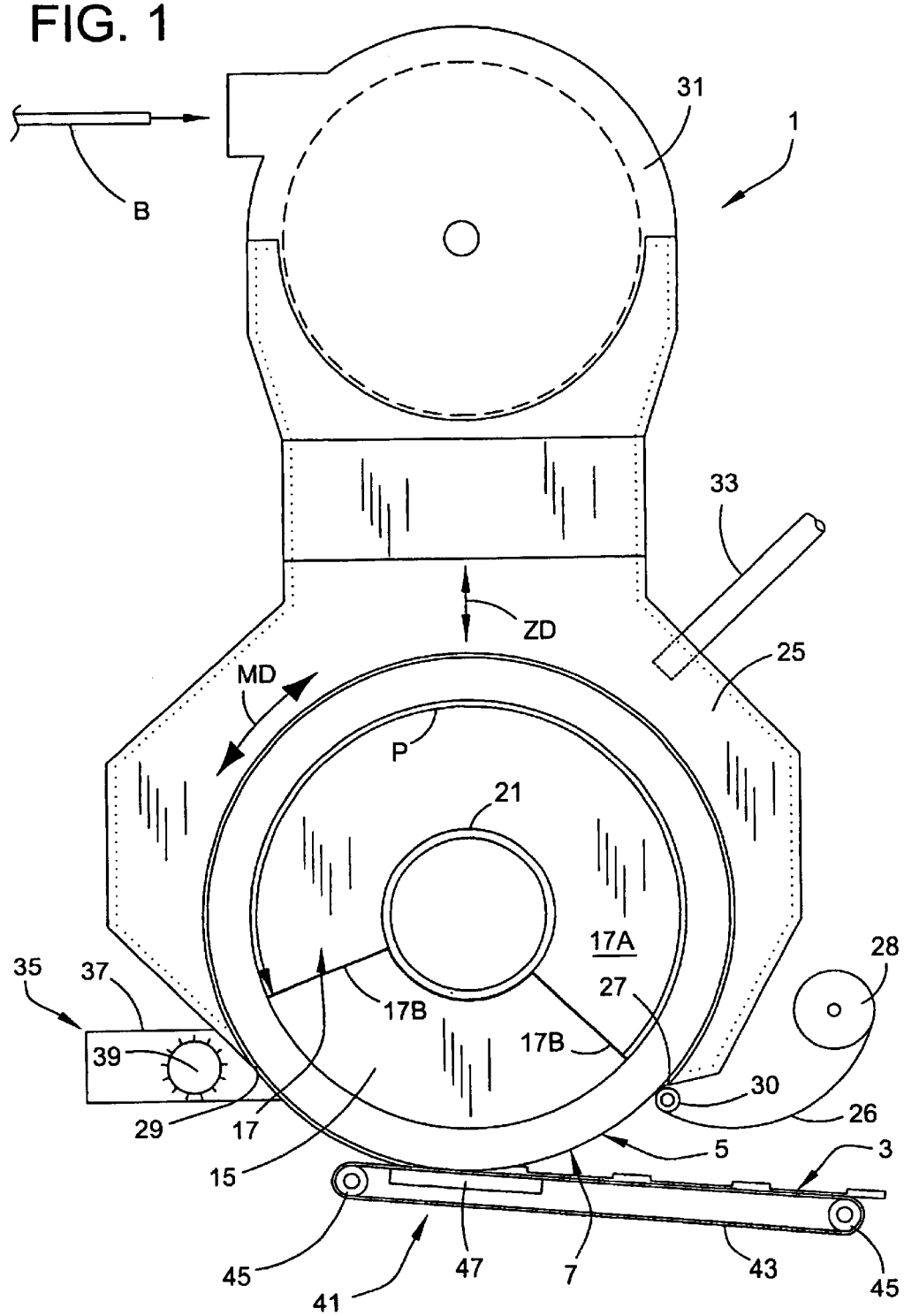
FIG. 1 is a schematic, side elevation of apparatus for forming an air formed fibrous web.
Figure 1A:
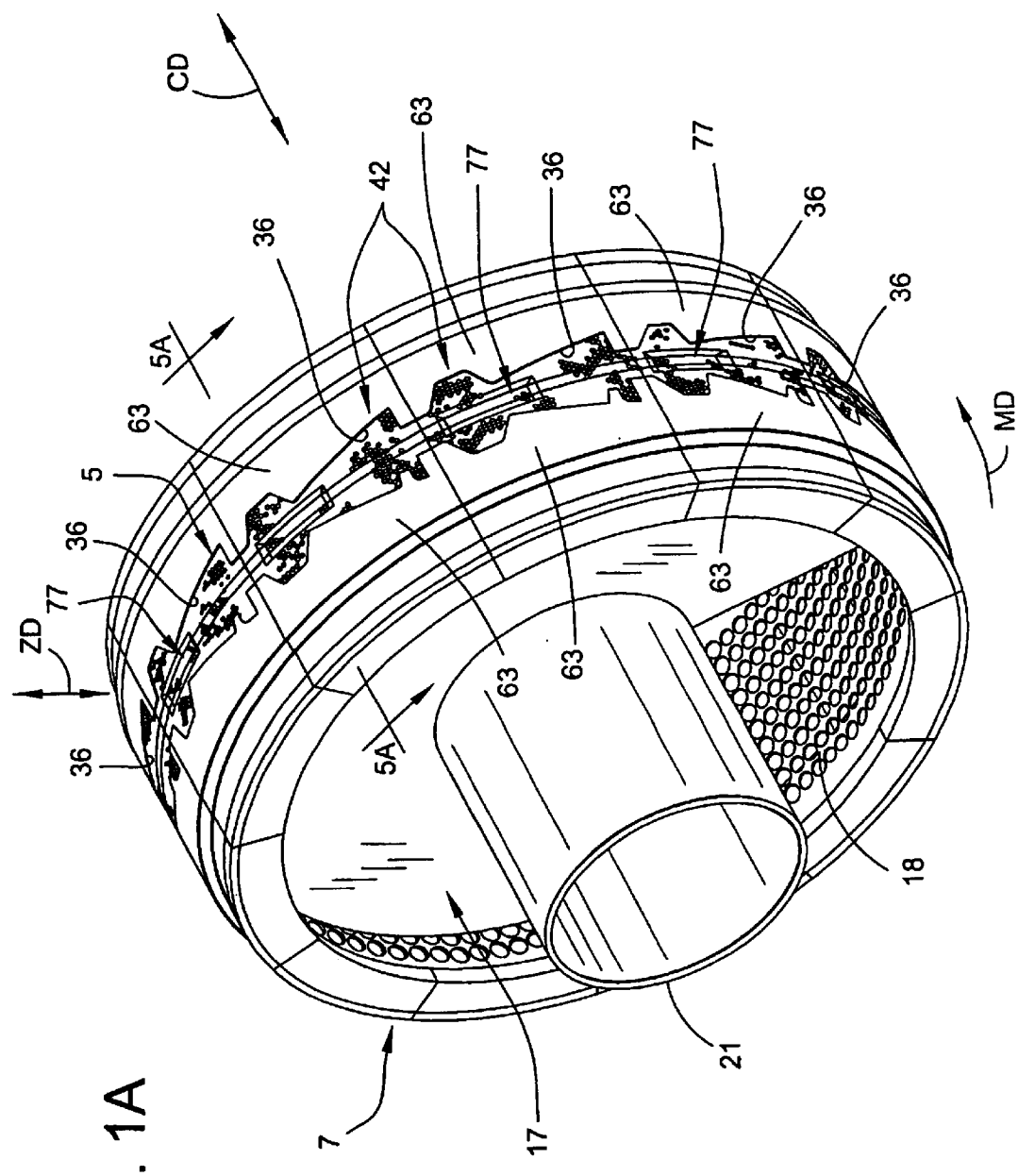
FIG. 1A is a schematic perspective of a drum of the apparatus.
Figure 2:
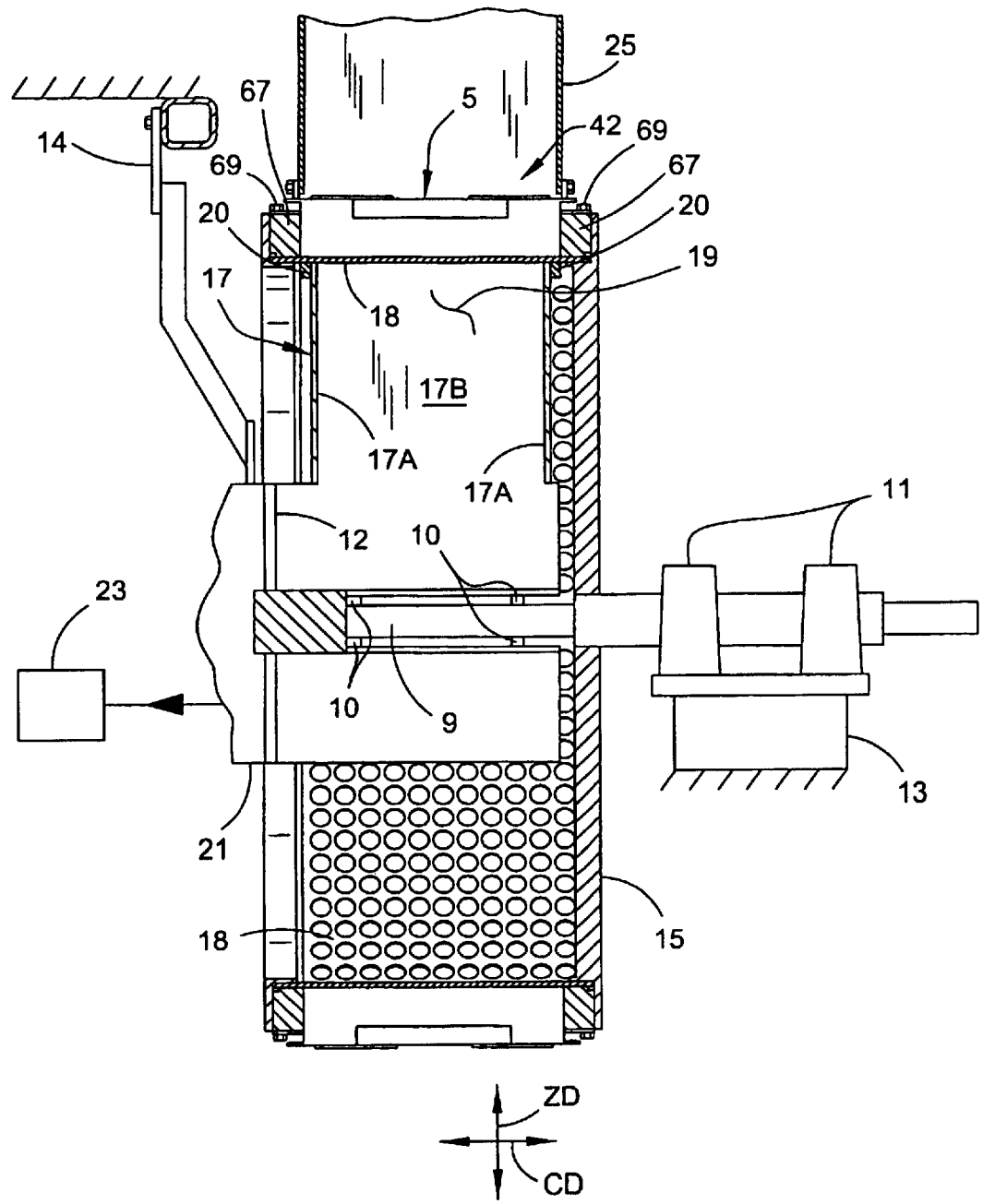
FIG. 2 is a fragmentary cross-section the apparatus of FIG. 1.

Referring to FIGS. 1, 1A and 2, for purposes of the present description, apparatus (indicated generally at 1) has a machine-direction MD which extends generally in the direction of motion of the machine, a lateral cross-direction CD which extends transversely to the machine direction, and a z-direction ZD. For the purposes of the present disclosure, the machine-direction MD is the direction along which a particular component or material is transported lengthwise along and through a particular, local position of the apparatus 1. The cross-direction CD lies generally within the plane of the material being transported through the process, and is transverse to the local machine-direction MD. The z-direction ZD is aligned substantially perpendicular to both the machine-direction MD and the cross-direction CD, and extends generally along a depth-wise, thickness dimension of the material.

Apparatus 1 constructed according to the principles of the present invention for forming a fibrous web 3 can include a movable, foraminous forming surface 5 extending around the circumference of a drum 7 (the reference numerals designating their subjects generally). The drum 7 is mounted on a shaft 9 connected by bearings 10 to a support 13. As shown in FIG. 2, the drum includes a circular wall 15 connected to the shaft 9 for conjoint rotation therewith. The shaft 9 is driven in rotation by a suitable motor or line shaft (not shown) in a counterclockwise direction as seen in FIG. 1. The wall 15 cantilevers the forming surface 5 and the opposite side of the drum 7 is open. A vacuum duct, indicated generally at 17, is located radially inwardly of the forming surface and extends over an arc of the drum interior. The vacuum duct 17 has an arcuate, elongate entrance opening 19 under the foraminous forming surface 5, as will be described in more detail hereinafter, for fluid communication between the vacuum duct and the forming surface. The vacuum duct 17 is mounted on and in fluid communication with a vacuum conduit 21 connected to a vacuum source 23 (represented diagrammatically in FIG. 2). The vacuum source 23 may be, for example, an exhaust fan. The vacuum duct 17 is connected to the vacuum supply conduit 21 along an outer peripheral surface of the conduit, and extends circumferentially of the conduit. The vacuum duct 17 projects radially outwardly from the vacuum conduit 21 toward the forming surface 5 and includes axially spaced side walls 17A and angularly spaced end walls 17B. The shaft 9 extends through the wall 15 and into the vacuum supply conduit 21 where it is received in bearings 10 connected to a brace 12 within the conduit. The bearings 10 are sealed with the vacuum supply conduit 21 so that air is not drawn in around the shaft 9 where it enters the conduit. The brace 12 and entire conduit 21 are supported by an overhead mount 14.

A drum rim 18 is mounted on the wall 15 of the drum 7 and has a multiplicity of holes over its surface area to provide a substantially free movement of air through the thickness of the rim. The rim 18 is generally tubular in shape and extends around the axis of rotation of the shaft 9 near the periphery of the wall 15. The rim 18 is cantilevered away from the drum wall 15, and has a radially inward-facing surface positioned closely adjacent to the entrance opening 19 of the vacuum duct 17. To provide an air resistant seal between the rim 18 and the entrance opening 19 of the vacuum duct 17, rim seals 20 are mounted on the inward-facing surface of the rim 18 for sliding sealing engagement with the walls 17A of the vacuum duct. Seals (not shown) are also mounted on the end walls 17B of the vacuum duct 17 for sliding sealing engagement with the inward-facing surface of the rim 18. The seals may be formed of a suitable material such as felt to permit the sliding sealing engagements.

The apparatus 1 further includes a forming chamber 25 through which the forming surface 5 is movable. The forming chamber 25 has an entrance 27 where the forming surface 5 enters the chamber substantially free of fibrous material, and an exit 29 where the forming surface leaves the chamber substantially filled with fibrous material. The forming surface 5 moves along a path P extending from the entrance 27 to the exit 29. A fiberizer 31 provides fibrous material into the forming chamber 25, and the vacuum source 23 (FIG. 2) creates a vacuum pressure in the vacuum duct 17 relative to the interior of the chamber 25. As the forming surface 5 enters and then traverses through the forming chamber 25, the component materials of the fibrous web 3 are operatively carried or transported by an entraining air stream that is drawn through the forming surface 5. The pressure differential across the forming surface 5 causes the fluent fibers in the chamber 25 to be drawn to the forming surface.

The selected fibrous material may be suitably derived from a batt B of cellulosic fibers (e.g., wood pulp fibers) or other source of natural and/or synthetic fibers, which has been disintegrated, in a manner well known in the art, to provide an operative quantity of individual, loose fibers. The fiberizer 31 receives a selected web-forming material, converts the web-forming material into individual fibers, and delivers the fibers into the forming chamber 25. In the illustrated configuration, the fiberizer 31 can be a rotary hammer mill or a rotatable picker roll. However, it is to be understood that fibers may be provided in other ways by other devices within the scope of the present invention. Suitable fiberizers are available from Paper Converting Machine Company, a business having offices located in Green Bay, Wis., U.S.A.

Other component materials for producing the fibrous web 3 may also be delivered into the forming chamber 25. For example, particles or fibers of superabsorbent material may be introduced into the forming chamber 25 by employing conventional mechanisms, such as pipes, channels, spreaders, nozzles and the like, as well as combinations thereof. In the illustrated embodiment, the superabsorbent material is delivered into the forming chamber 25 by employing a schematically represented delivery conduit and nozzle system 33. The fibers, particles and other desired web material may be entrained in any suitable fluid medium. Accordingly, any references herein to air as being the entraining medium should be understood to be a general reference which encompasses any other operative entraining fluid. Superabsorbent materials are well known in the art, and are readily available from various suppliers. For example, FAVOR SXM 880 superabsorbent is available from Stockhausen, Inc., a business having offices located in Greensboro, N.C. U.S.A.; and DRYTECH 2035 is available from Dow Chemical Company, a business having offices located in Midland, Mich., U.S.A.

The stream of fluent fibers and particles pass through the forming chamber 25 for deposition onto the forming surface 5. The forming chamber 25 can serve to direct and concentrate the air-entrained fibers and particles, and to provide a desired velocity profile in the air-entrained stream of fibers and particles. Typically, the forming chamber 25 is supported by suitable structural members, which together form a support frame for the forming chamber. The frame may be anchored and/or joined to other suitable structural components, as necessary or desirable. The construction and operation of such forming chambers 25 is well known and will not be described in further detail herein.

To produce a reinforced absorbent article, such as an absorbent core of a disposable diaper, child's training pants, feminine care article, incontinence article, bandage and the like, a reinforcing member such as a continuous web of scrim 26 is applied to the forming drum 7 for integration with the fibrous web 3. A web of scrim 26 is shown in FIG. 1 to extend from a roll 28 onto the forming drum 7 at the entrance 27 of the forming chamber 25. The roll 28 can be held and the scrim 26 fed out by suitable delivery device (not shown in its entirety) as is known in the art. A roller 30 of the delivery device is shown for guiding the web of scrim 26 into the entrance 27. The scrim 26 overlies at least a portion of the forming surface 5 within the forming chamber 25.

Figure 4:
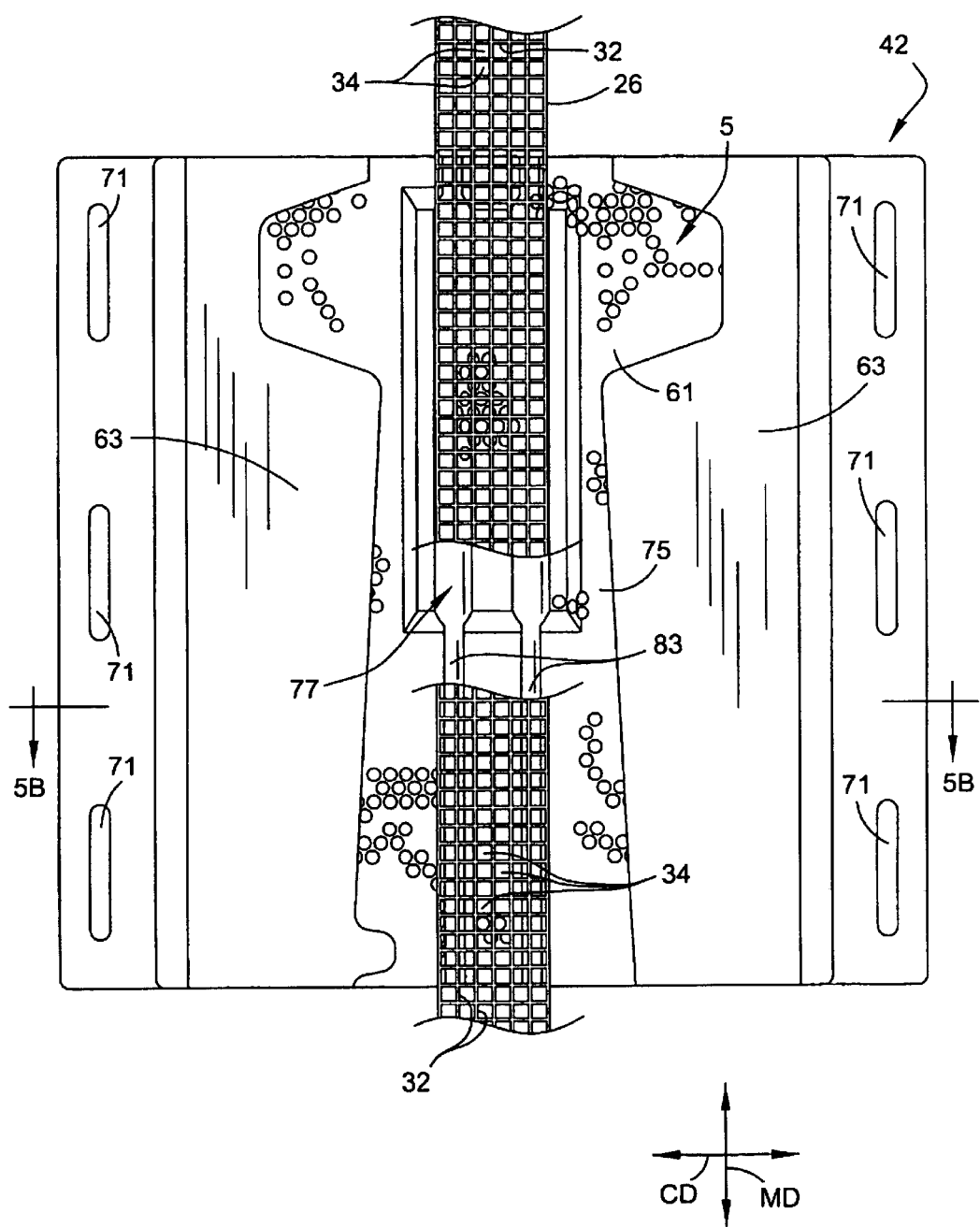
FIG. 4 is a top plan view of the form member.

The web of scrim 26 (broadly, "a reinforcing member") is incorporated into the fibrous web 3 formed by the apparatus 1. Referring to FIG. 4, the scrim 26 comprises elongate strands 32 which are arranged so that the strands cross each other. More specifically, the strands 32 are arranged in a grid including parallel strands extending in the longitudinal (or "machine") direction MD and strands extending in the lateral (or "cross") direction CD defining rectangular openings 34 in the scrim. However, the openings may have shapes other than rectangular without departing from the scope of the present invention. Among other things, the openings 34 permit liquid to flow substantially unhindered through the scrim 26. The strands 32 are secured to each other where they intersect to create a lattice providing strength and stability to the absorbent core.

The scrim 26 can be made of any suitable material that provides desired levels of strength and flexibility. For example, the strands 32 of the scrim 26 may be composed of natural or synthetic materials, as well as combinations thereof. In a particular arrangement, the material of the strands 32 may include a synthetic polymer (e.g., polyester, polyethylene, polypropylene, nylon, rayon). The synthetic polymer may be monofilament, bicomponent or multicomponent. One conventional way to form scrim of such material is to extrude and orient strands to form a net configuration. Another way of forming such material is by a photomasking process. In that process, a photosensitive resin is deposited on a woven fabric. A mask is applied in the form of the scrim and electromagnetic radiation is used to cure the unmasked portions of the resin. The mask is then removed and the uncured portions of the resin are washed away, leaving the scrim-patterned, cured resin. Natural materials that could be used include cotton, jute, hemp, wool. Alternate materials include glass, carbon and metallic fibers. The reinforcing scrim 26 can be a woven or nonwoven material. The scrim strands in the longitudinal and lateral directions could be of different materials. Alternately different materials could be used in alternating scrim strands in the longitudinal and/or lateral direction. In one embodiment, the strands 32 may be formed of superabsorbent material. In that event, the scrim 26 would serve a liquid retention function in addition to its reinforcing function. Still further, the scrim 26 could be formed of one material and coated with another material, or be a biodegradable material, such as polylactic acid. An example of a superabsorbent coating is given in co-assigned application Ser. No. 10/246,811 entitled ABSORBENT ARTICLES HAVING A SUPERABSORBENT RETENTION WEB by Newbill et al., filed Sep. 18, 2002 (attorney docket No. 16,739), the disclosure of which is incorporated herein by reference.

A reinforcing member of the same type as the scrim 26 of the present invention is shown and described in co-assigned U.S. patent application Ser. No. 10/306,086 entitled ABSORBENT ARTICLE WITH REINFORCED ABSORBENT STRUCTURE by D. Heyn et al. and U.S. patent application Ser. No. 10/306,185 entitled ABSORBENT ARTICLE HAVING DISCONTINUOUS ABSORBENT CORE by S. Melius et al. filed on Nov. 27, 2002 simultaneously herewith. The disclosures of these applications are incorporated herein by reference. It is noted that the reinforcing member may take forms (not shown) other than scrim 26 without departing from the scope of the present invention. For example, the reinforcing member could be perforated film or even a solid material capable of providing reinforcement of the fibrous web 3. Moreover, the reinforcing member could be formed by multiple pieces and/or multiple layers of reinforcing material.

The forming surface 5 is illustrated as being part of the forming drum 7, but it is to be understood that other techniques for providing the forming surface may also be employed without departing from the scope of the present invention. For example, the forming surface 5 may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

The foraminous forming surface 5 is defined in the illustrated embodiment by a series of form members 42 which are arranged end-to-end around the periphery of the forming drum 7 and independently attached to the drum. As may be seen in FIG. 1A, the form members 42 of the first embodiment each define a substantially identical pattern 36 in which fibrous material is deposited. The patterns 36 correspond to a desired shape of individual absorbent cores 38 (one of which is shown in cross section in FIG. 6) which repeats over the circumference of the drum 7. However, partially repeating or non-repeating pattern shapes may be used with the present invention. Under the influence of the vacuum source 23, a conveying air stream is drawn through the foraminous forming surface 5 into the vacuum duct 17 on the interior of the forming drum 7, and is subsequently passed out of the drum through the vacuum supply conduit 21. As the fluent fibers and particles impinge the foraminous forming surface 5 and the scrim 26, the air component is passed through the forming surface and scrim, and the fibers-particles component is retained by the forming surface (and/or scrim) to form the nonwoven fibrous web 3. Subsequently, with the rotation of the drum 7, the formed web 3 is removed from the forming surface 5.

The forming surface 5 carrying the air formed fibrous web 3 and scrim 26 passes out of the forming chamber 25 through the exit 29 to a scarfing system, generally indicated at 35 in FIG. 1, where excess thickness of the fibrous web can be trimmed and removed to a predetermined extent. The scarfing system includes a scarfing chamber 37 and a scarfing roll 39 which is positioned within the scarfing chamber. The scarfing roll 39 abrades excess fibrous material from the fibrous web 3, and the removed fibers are transported away from the scarfing chamber 37 with a suitable discharge conduit (not shown), as well known in the art. The removed fibrous material may, for example, be recycled back into the forming chamber 25 or the fiberizer 31, as desired. Additionally, the scarfing roll 39 can rearrange and redistribute fibrous material along the longitudinal machine-direction MD of the web 3 and/or along the lateral cross-direction CD of the web. The profile of the web 3 made by a scarfing roll may be flat (as with scarfing roll 39), but also may be shaped or irregular as desired by selection and arrangement of teeth on the scarfing roll. In like manner, any other suitable trimming mechanism may be employed in place of the scarfing system 35 to provide a cutting or abrading action to the air formed fibrous web 3 by a relative movement between the fibrous web and the selected trimming mechanism.

After the scarfing operation, the portion of the forming surface 5 that is carrying the air formed fibrous web 3 can be moved to a release zone of the apparatus 1. In the release zone, vacuum causes the web 3 (incorporating the scrim 26) to transfer from the forming surface 5 onto a conveyor indicated generally at 41. The release can be assisted by the application of air pressure from the interior of the drum 7. The conveyor 41 receives the formed fibrous web 3 from the forming drum 7, and conveys the web to a collection area or to a location for further processing (not shown). Suitable conveyors can, for example, include conveyer belts, vacuum drums, transport rollers, electromagnetic suspension conveyors, fluid suspension conveyors or the like, as well as combinations thereof. In the illustrated embodiment, the conveyor 41 includes an endless conveyor belt 43 disposed about rollers 45. A vacuum suction box 47 is located below the conveyor belt 43 to remove the web 3 from the forming surface 5. The belt 43 is perforate and the vacuum box 47 defines a plenum beneath the portion of the belt in close proximity to the forming surface so that a vacuum is communicated to the fibrous web 3 on the drum 7. Removal of the web 3 can alternatively be accomplished by the weight of the web, by centrifugal force, by mechanical ejection, by positive air pressure or by some combination or by another suitable method. The positive air pressure can be produced, for example, by a source of compressed air (not shown) such as a fan which generates a pressurized air flow that exerts a force directed outwardly through the forming surface 5. The removed fibrous web 3 comprises an interconnected series of absorbent cores 38, and each core has a selected surface contour which substantially matches the contour provided by the corresponding portions of the forming surface 5 upon which each individual core was formed.

Suitable forming drum systems for producing air formed fibrous webs are well known in the art. For example, see U.S. Pat. No. 4,666,647 entitled APPARATUS AND METHOD FOR FORMING A LAID FIBROUS WEB by K. Enloe et al. which issued May 19, 1987; U.S. Pat. No. 4,761,258 entitled CONTROLLED FORMATION OF LIGHT AND HEAVY FLUFF ZONES by K. Enloe which issued Aug. 2, 1988; and U.S. patent application Ser. No. 10/207,929 entitled APPARATUS AND FORM FOR MAKING AN AIR FORMED FIBROUS WEB by Venturino et al., filed Jul. 30, 2002 the entire disclosures of which are incorporated herein by reference. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, and U.S. patent application Ser. No. 09/947,128, entitled MULTI-STAGE FORMING DRUM COMMUTATOR by D. P. Murphy et al., filed Sep. 4, 2001, the entire disclosures of which are incorporated herein by reference. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith. It will be appreciated that the description of the drum 7 shown in the drawings is exemplary, as other configurations (including those not having a drum for carrying the foraminous forming surface 5) may be employed to produce the fibrous web 3.

Figure 3:
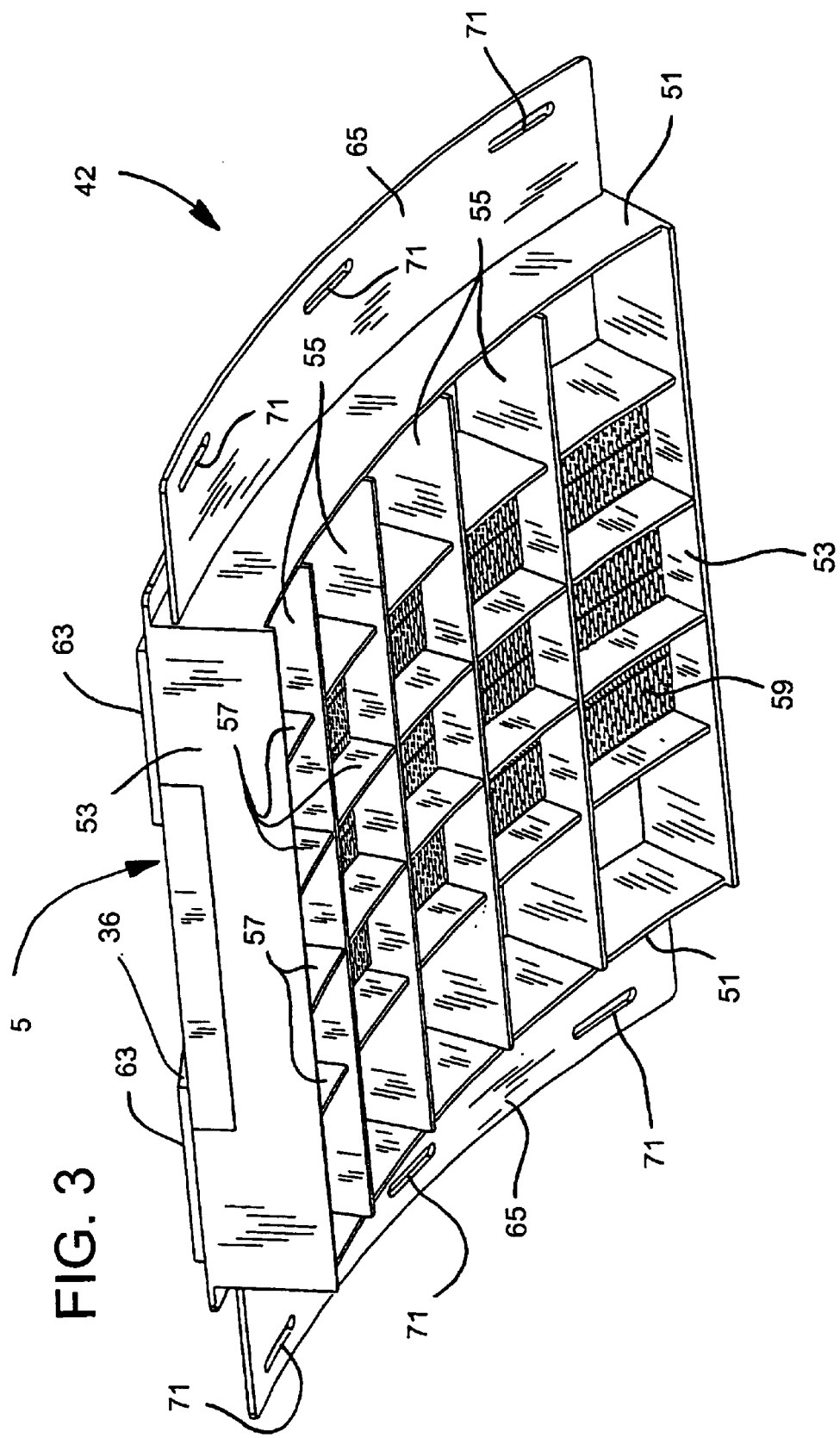
FIG. 3 is a bottom perspective of a form member of the apparatus.
Figure 5A:
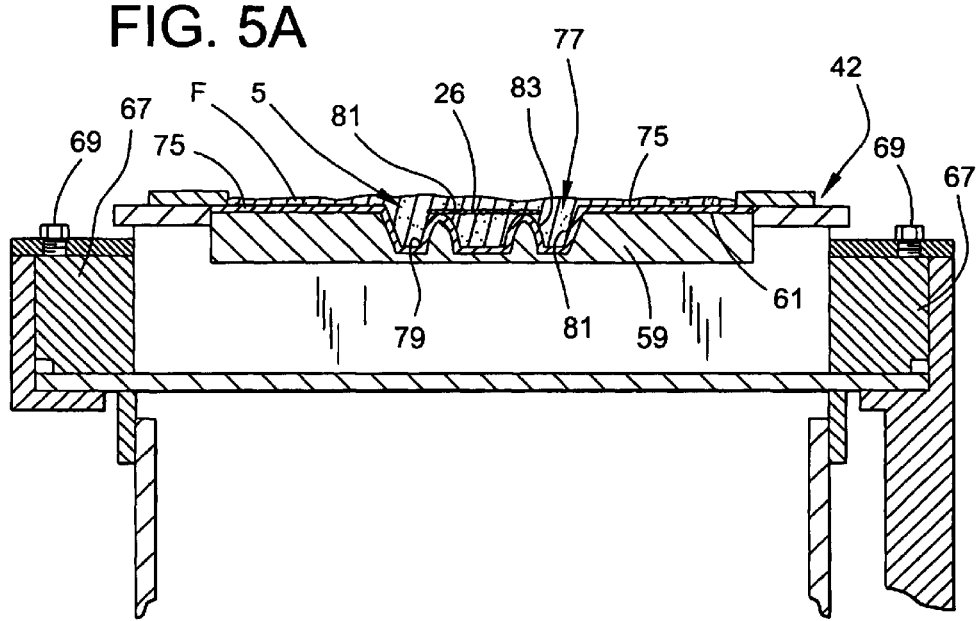
FIG. 5A is a fragmentary section taken in the plane including line 5A—5A of FIG. 1A and illustrating the placement of reinforcing scrim on the form member.
Figure 5B:
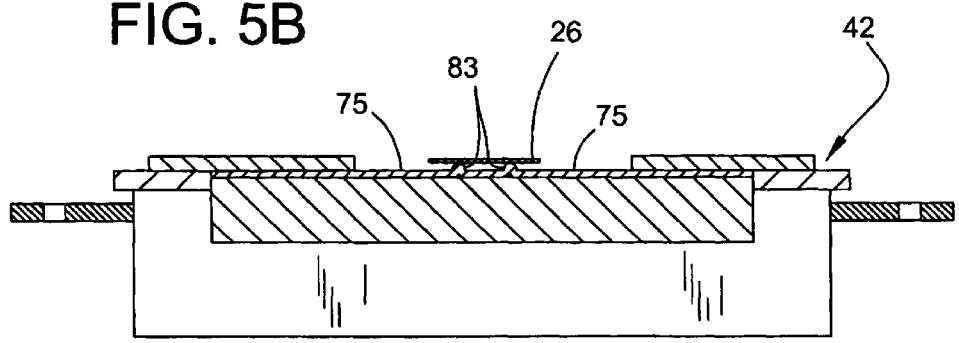
FIG. 5B is a section taken in the plane including line 5B—5B of FIG. 4 and illustrating the placement of reinforcing scrim at a different location on the form member.

Referring now to FIG. 3, a single form member 42 is shown as removed from the drum 7. As used herein, the term "form" can refer to a single form member 42 or to a collection of form members, such as the form members which extend around the complete circumference of the drum 7. Moreover, it is envisioned that a single form member (not shown) extending around the entire circumference of the drum 7 could be employed. The illustrated form member 42 comprises outer side walls 51 connected to end walls 53 to form a rectangular frame. Transverse walls 55 extend in the cross direction CD between the side walls 51 and longitudinal walls 57 extend in the machine-direction MD between the end walls 53 inside the frame. The side walls 51 and longitudinal walls 57 are curved along their length to match the arc of the drum 7 over which the individual form members 42 will extend. The frame supports the forming surface 5, which in the illustrated embodiment comprises a honeycombed support 59 and a thin, perforated plate 61 (see FIGS. 4 and 5). Although the plate 61 has a regular pattern of openings over substantially its entire area, only a few openings are illustrated for convenience in the drawings. The support 59 and perforated plate 61 have the same upper surface shape. The support 59 underlies and provides strength for the perforated plate 61 to hold it in a fixed configuration under the load applied by the vacuum. The support 59 permits air to pass freely through it by virtue of the relatively larger openings of its honeycomb structure. The openings can have any desired cross-sectional shape, such as circular, oval, hexagonal, pentagonal, other polygonal shape or the like, as well as combinations thereof, and need not be in a honeycomb arrangement. Such support structures are well known in the art, and can be composed of various materials, such as plastic, metal, ceramics and the like, as well as combinations thereof. The smaller holes in the perforated plate 61 also allow passage of air, but are sized to capture the fibrous material and prevent its passage through the forming surface 5. The perforate plate 61 may be replaced by screen, a wire mesh, a hard-wire cloth or the like, as well as combinations thereof. It is envisioned that if a sufficiently rigid, self-supporting material could be found for the perforated plate 61, the support 59 could be omitted.

Masking plates 63 are attached to the radially outwardly facing surface of the form member 42 to mask portions of the perforated plate 61 and support 59 to prevent air from passing through the masked portions and hence prevent deposition of fibrous material. The patterns 36 are defined by the shape of the masking plates 63. The form member 42 is mounted on the drum 7 by a pair of wings 65 attached to and extending laterally outwardly from respective side walls 51. When applied to the drum 7 as shown in FIG. 2, the wings 65 of the form member 42 overlie respective, axially spaced mounting rings 67 mounted on the rim 18 at its opposite lateral edges. The form member 42 is releasably secured to the mounting rings 67 by bolts 69 passing through elongate openings 71 in the wings and threadably received in holes (not shown) formed in the rings. The elongation of the openings 71 allows some variation in the circumferential position of the form member 42, facilitating placement of the form members on the drum 7.

Referring now to FIG. 4, the single form member 42 from the drum 7 is shown from the top. The forming surface 5 has a length in the machine direction MD and a width in the cross direction CD and is shaped to include a first section 75 at a first depth below the top surface of the masking plate 63. The first section 75 is relatively shallow and planar in configuration for forming a thinner layer of fibrous material. The first section 75 is curved between the longitudinal ends of the form member 42 in correspondence with the curvature of the drum 7. Thus rather than being truly planar, the first section 75 lies in a smooth surface and is substantially linear in cross section, as may be seen in FIGS. 5A and 5B. It will be noted that the cross section is transverse to the extent of the form member 42 in the machine direction MD. However, the first section 75 may be irregular or have different depths over its area without departing from the scope of the present invention. In that event the "first depth" would be an average depth of the first section 75.

A pocket, indicated generally at 77, includes a bottom surface 79 ("second section") and a transition surface ("third section") connecting the first section 75 with the bottom surface. The terms "top", "bottom", "higher", "lower" and the like are used as convenient descriptors given the orientations illustrated in the drawings. However, these terms as used in the specification or claims, do not require any absolute orientation of the subject described. The first section 75 includes portions lying on both sides of the bottom surface 79. The pocket 77 extends lengthwise of the forming surface 5 and is surrounded by the shallower first section 75. However, it is to be understood that a pocket (not shown) may extend continuously the full length of the forming surface 5 without parting from the scope of the present invention. The scrim 26 is shown in FIG. 4 as extending beyond the form member 42. In use, the scrim 26 would extend continuously from one form member 42 to the next on the drum 7. The bottom surface 79 (as shown in FIGS. 4 and 5) has a generally undulating configuration which is everywhere below the surface containing the first section 75, and is non-linear in cross section. More particularly, the bottom surface 79 has multiple ridges 83 extending in the machine direction MD the length of the pocket 77. As a result of the ridges 83, the (second) depth of the bottom surface 79 below the first section 75 varies over the area of the bottom surface. The pocket 77 is closely similar to the one disclosed in co-assigned U.S. application Ser. No. 10/207,929.

The ridges 83 located within the pocket 77 greatly increase the surface area within the pocket, reducing resistance to air flow (as compared to the first section 75) and thereby promoting the deposit of more fibrous material F. As a result of the surface area of the bottom surface 79, the depth of fibrous material F deposited in the pocket 77 is significantly greater than in the first section 75. The openings 34 of the scrim 26 permit passage of fibers and particles into the bottom of the pocket 77 so that the pocket can be filled with fibers and other particulates (e.g., superabsorbent material). Some of the fibers become entangled with the strands 32 of the scrim 26. Still other fibers become entangled with each other through the scrim 26, or become entangled with fibers previously entangled on strands 32 of the scrim. In this way, the scrim 26 becomes integrated with the fibrous material F to strongly reinforce the fibrous web 3. However, it is to be understood that other ways of interconnecting the scrim 26 with the fibers may be used, such as adhesive bonding or fusion, without departing from the scope of the present invention.

Figure 6:
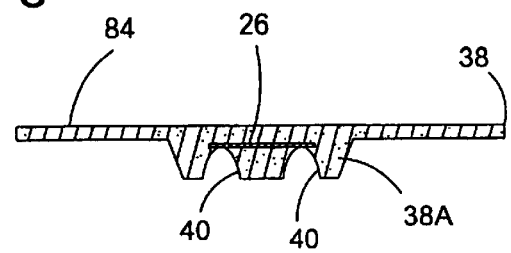
FIG. 6 is a cross section of a scarfed absorbent core formed by apparatus of the present invention and including reinforcing scrim.

When the fibrous web 3 is scarfed and cut to define absorbent cores like the absorbent core 38 illustrated in FIG. 6, a liquid holding formation 38A of the absorbent core has its full specified thickness and an upper surface 84 which is substantially flat. In other words, there is no dip in the upper surface 84 of the scarfed absorbent core 38 in the area of the liquid holding formation 38A caused by inadequate deposition of fibrous material F in the pocket 77 of the forming surface 5. The liquid holding formation 38A is reinforced by the embedded scrim 26. The screen side of the liquid holding formation 38A (i.e., the side which engages the forming surface 5 when formed) is formed by the ridges 83 to have two channels 40 extending the length of the pocket 77. It is to be understood that greater or fewer than two channels could be formed. Referring to FIGS. 5 and 6, the surface area of the liquid holding formation 38A on the screen side of the absorbent core 38 is augmented by the shape given to it by the ridges 83 of the forming surface 5.

Moreover, the ridges 83 (broadly, "support formations") contact and locate the scrim 26 in the thickness or z-direction ZD of the fibrous web 3. As may be seen in FIGS. 4, 5A and 5B, the scrim 26 rests on top of the ridges 83 and is thereby positioned in the z-direction ZD with respect to the forming surface 5. The z-direction location is selected so that the scrim 26 is adequately embedded for strength and reinforcement, and to avoid contact with the scarfing roll 39. In the illustrated embodiment, the bottom surface 79 includes lowermost portions (i.e., at the bases of the ridges 83). The ridges locate the scrim 26 above these lowermost portions of the bottom surface 79. Outside of the pocket 77 the height of the ridges 83 is greatly reduced, as may be seen in FIG. 5B. A thinner section of the absorbent core 38 is formed in first section 75 outside the pocket 77, so that the scrim 26 is positioned much closer to the floor of the forming surface 5 and the ridges 83 are shorter. No additional support or location structure other than the ridges 83 for the scrim 26 is needed, although the use of such additional structure would not depart from the scope of the present invention. Moreover, although the ridges 83 are shown to extend continuously lengthwise of the forming surface 5, they may be discontinuous. The ridges 83 beneficially serve both a function of shaping the fibrous web 3 and locating the scrim 26.

The web of scrim 26 may pass directly from the roller 30 onto the forming surface 5 prior to passage of the forming surface through the entrance 27 into the forming chamber 25. It is not necessary for a layer of fluff ("fluidized fibers") to be deposited on the forming surface 5 prior to the scrim 26 because the fluff is not needed to space the scrim off of the bottom of the forming surface. In general, the scrim might be placed on the forming surface 5 at locations ranging from prior to entering the forming chamber 25 to a location within the forming chamber about 25% of the length of the path P from the entrance 27. In another embodiment, the scrim 40 is placed on the forming surface 5 at a location about 15% of the way along the path P from the entrance 27 of the forming chamber. The vacuum drawn within the drum 7, and tension in the web of scrim 26 holds the scrim against the forming surface 5. The position of the scrim 26 in the z-direction ZD is selected by the height of the ridges 83. It will be understood that the z-direction position could be changed by forming ridges (not shown) of a different height than those shown in FIGS. 5A and 5B. It will also be appreciated that a greater or lesser number of ridges may be used to support the scrim. Moreover, the structure which supports the scrim 26 in a selected position within the thickness of the web 3 need not be a ridge. Other examples of such supporting structure will be described hereinafter.

Figure 7:
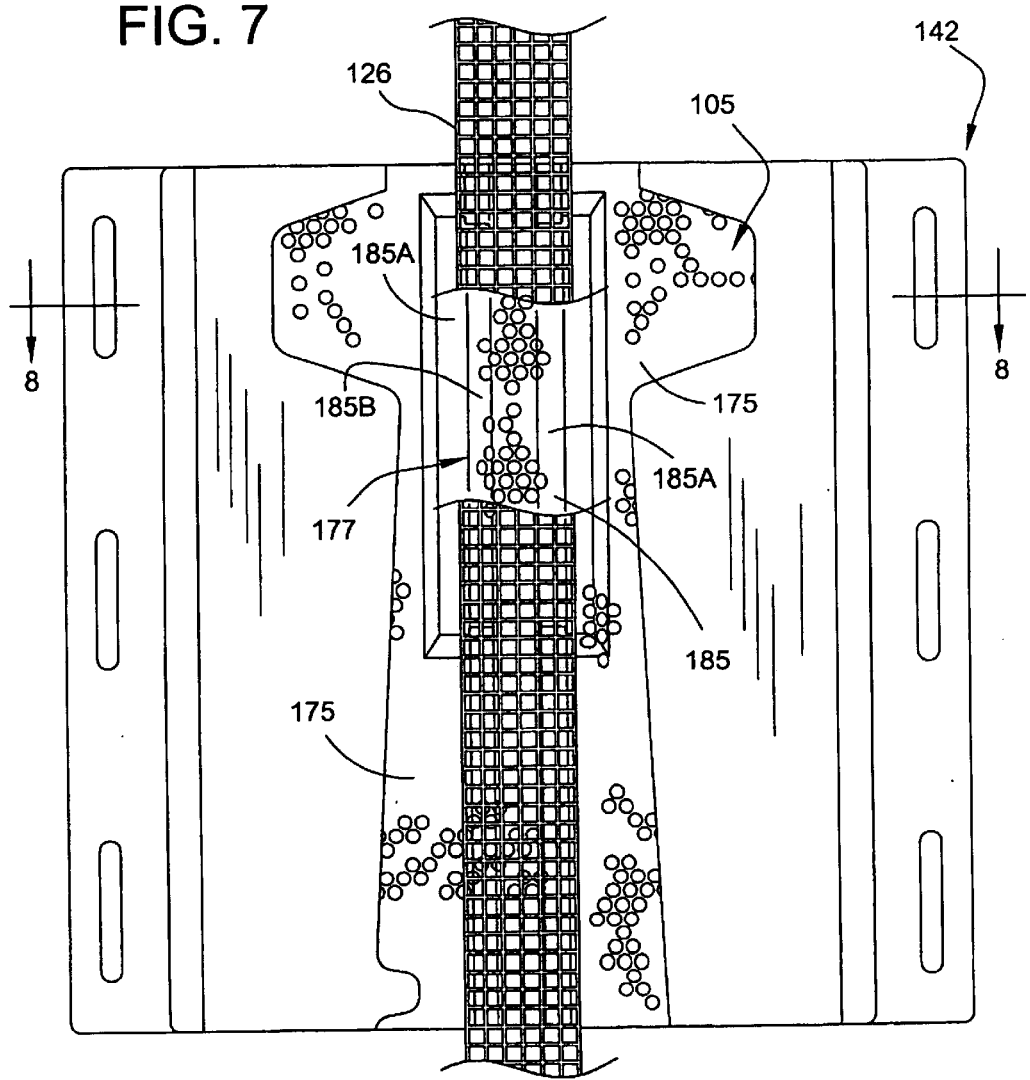
FIG. 7 is a top plan view of a form member of a second embodiment.
Figure 8:
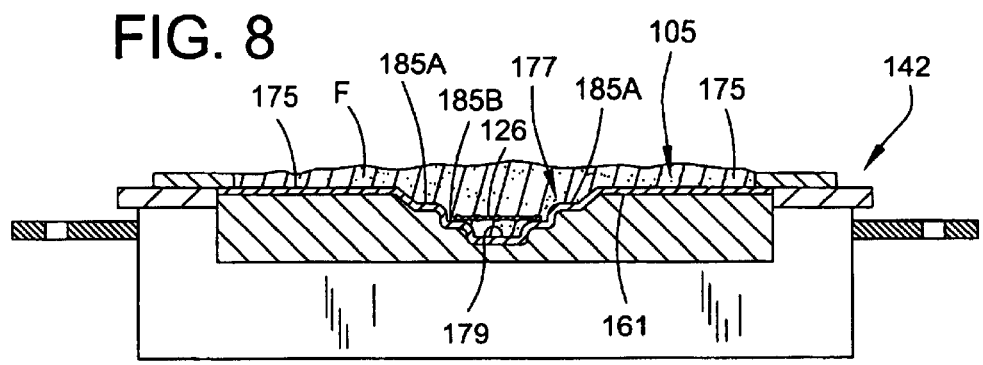
FIG. 8 is a section taken in the plane including line 8—8 of FIG. 7 and illustrating the placement of reinforcing scrim on the form member.

A form member 142 of a second embodiment having a forming surface 105 is shown in FIGS. 7 and 8. Corresponding parts of the form member 142 of the second embodiment will be indicated by the same reference numerals as for the form member 42 of the first embodiment, plus "100". The forming surface 105 includes a first section 175 substantially the same as the first section 75 of the forming surface 5 of FIG. 4. A pocket 177 includes a transition surface connecting the first section 175 to a bottom surface 179 of the pocket. However instead of ridges 83, the bottom surface 179 includes two sets of steps 185A and 185B (broadly, "support formations") extending in the machine-direction of the pocket 177 which contact and support the scrim 126. The provision of the stepped bottom surface 179 within the pocket 177 increases the surface area of the pocket so that more fibrous material F will be deposited in the pocket before the region of the perforated plate 161 within the pocket becomes obstructed with fibrous material.

In the second embodiment of the form member 142, the lower two steps 185B provide the support structure for the scrim 126 (see FIG. 8). The steps 185B locate the scrim 126 in the thickness or z-direction ZD in the fibrous web. The other steps 185A could be used to locate a wider web of scrim 126. Moreover, the steps 185A are formed for contacting longitudinal edge margins of the scrim 126 to locate it in the cross-direction CD. It is to be understood that structure other than steps could be employed to contact the scrim 126 for locating in the cross-direction CD. The number of steps 185A, 185B, and their configurations could be other than shown to, for example, change the z-direction ZD and/or cross-direction CD location of the scrim 126 within the fibrous material F.

Figure 10:
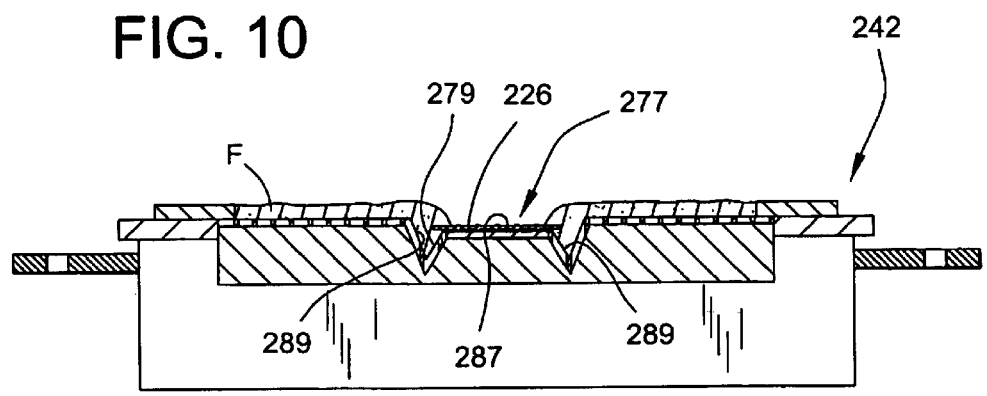
FIG. 10 is a section taken in the plane including line 10—10 of FIG. 9 and illustrating the placement of reinforcing scrim on the form member.
Figure 9:
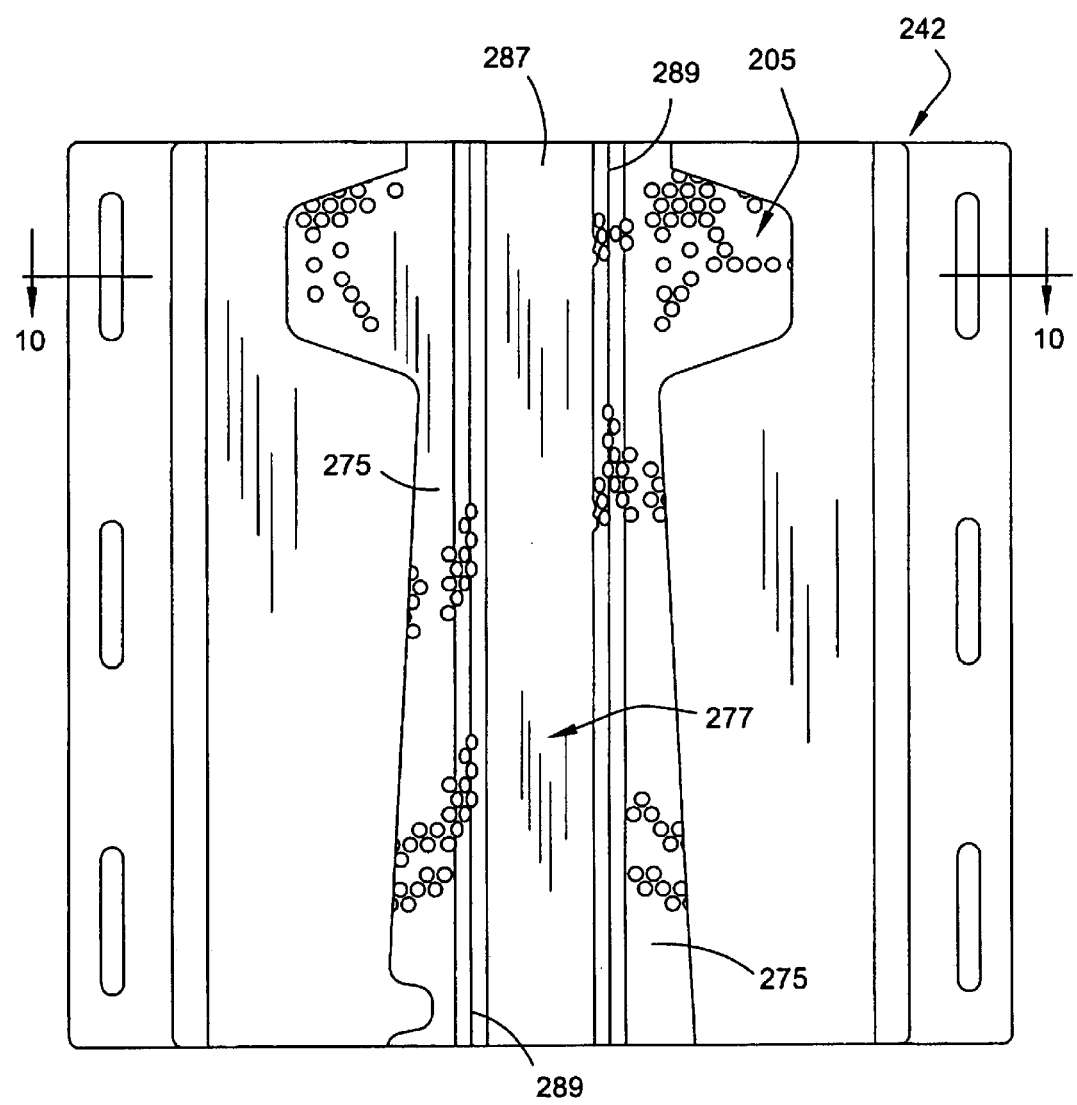
FIG. 9 is a top plan view of a form member of a third embodiment.
Figure 11:
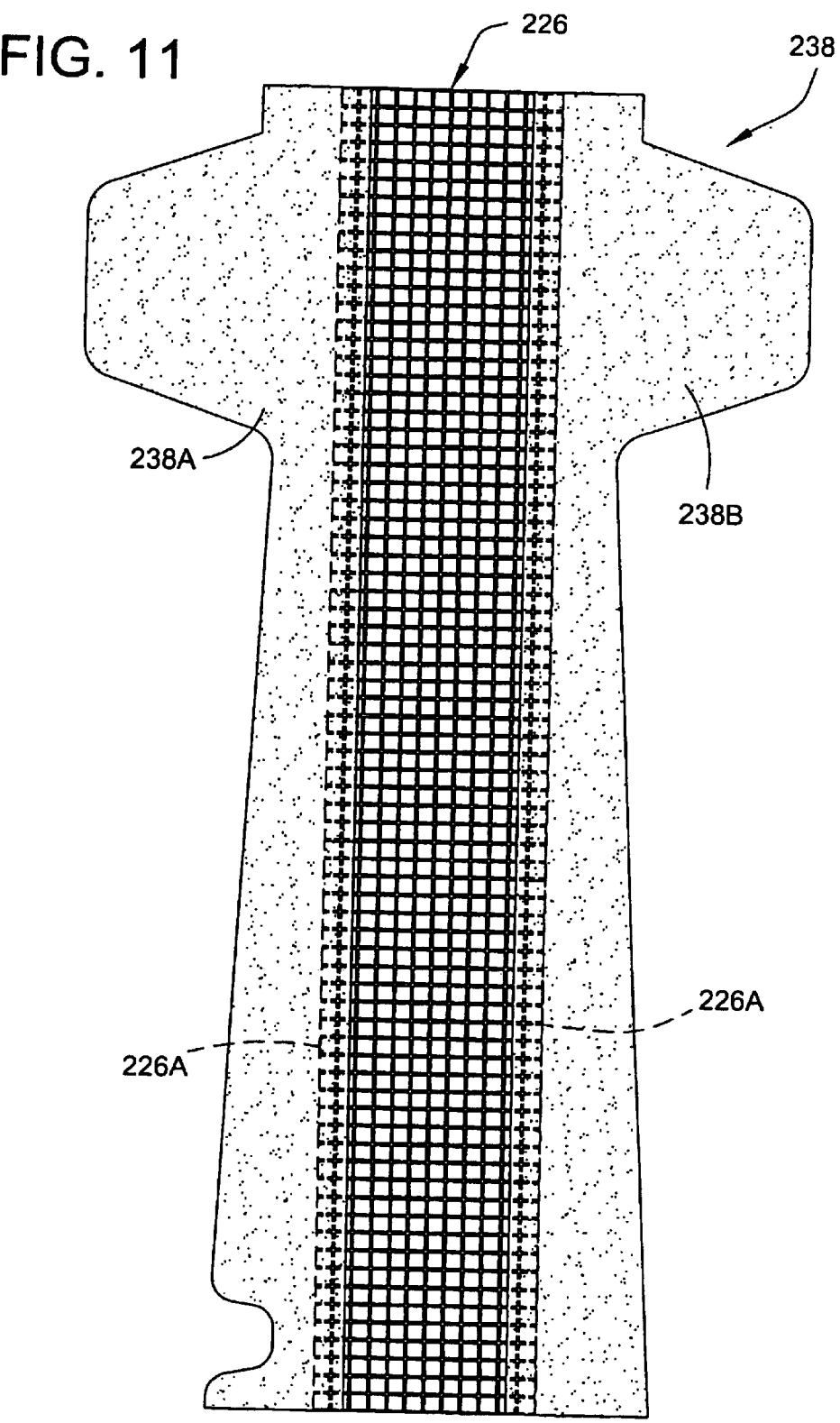
FIG. 11 is an absorbent core produced using the form member of FIG. 9.

A third embodiment of the form member 242, shown in FIGS. 9 and 10, may be used to form a ventilated absorbent core 238 (FIG. 11). Reinforced ventilated absorbent cores of this type are shown in co-assigned U.S. application Ser. No. 10/306,185 entitled ABSORBENT ARTICLE HAVING DISCONTINUOUS ABSORBENT CORE by S. Melius et al. field on Nov. 27, 2002. Corresponding parts of the third embodiment of the form member 242 will be indicated by the same reference numerals as for the first embodiment of the form member 42, plus "200". The forming surface 205 includes a first section 275 substantially the same as the first section 75 of the forming surface 5 of FIGS. 4 and 5. A bottom surface 279 of a pocket 277 comprises a central plateau 287 (broadly "a support formation") and generally V-shaped channels 289 on either side of the plateau. The plateau 287 is solid, meaning that there are no perforations or holes which permit the passage of air through the plateau. Accordingly, fibers and particles are not drawn onto the plateau 287 and two laterally separated fibrous web sections (corresponding to absorbent core sections 238A, 238B) are formed by the forming surface 205.

As shown in FIG. 10, the central plateau 287 contacts and locates the scrim 226 at a selected position in the z-direction ZD of the forming surface 205 of the form member 242. The scrim 226 is wider than the plateau 287 so that longitudinal edge margins 226A of the scrim 226 overhang the V-shaped channels 289. The channels have openings for the passage of air so that fibers and particles are drawn into them. The longitudinal edge margins 226A overhanging the channels 289 become attached to respective fibrous web sections (i.e., core sections 238A, 238B) through fiber entanglement or in another suitable manner, as described above. Accordingly, the absorbent core sections 238A, 238B are interconnected by the scrim 226. The central region of the absorbent core 238 is formed exclusively by the scrim 226 so that air and vapor may pass readily through the absorbent core in this region, even after the core has received one or more insults.

Figure 12:
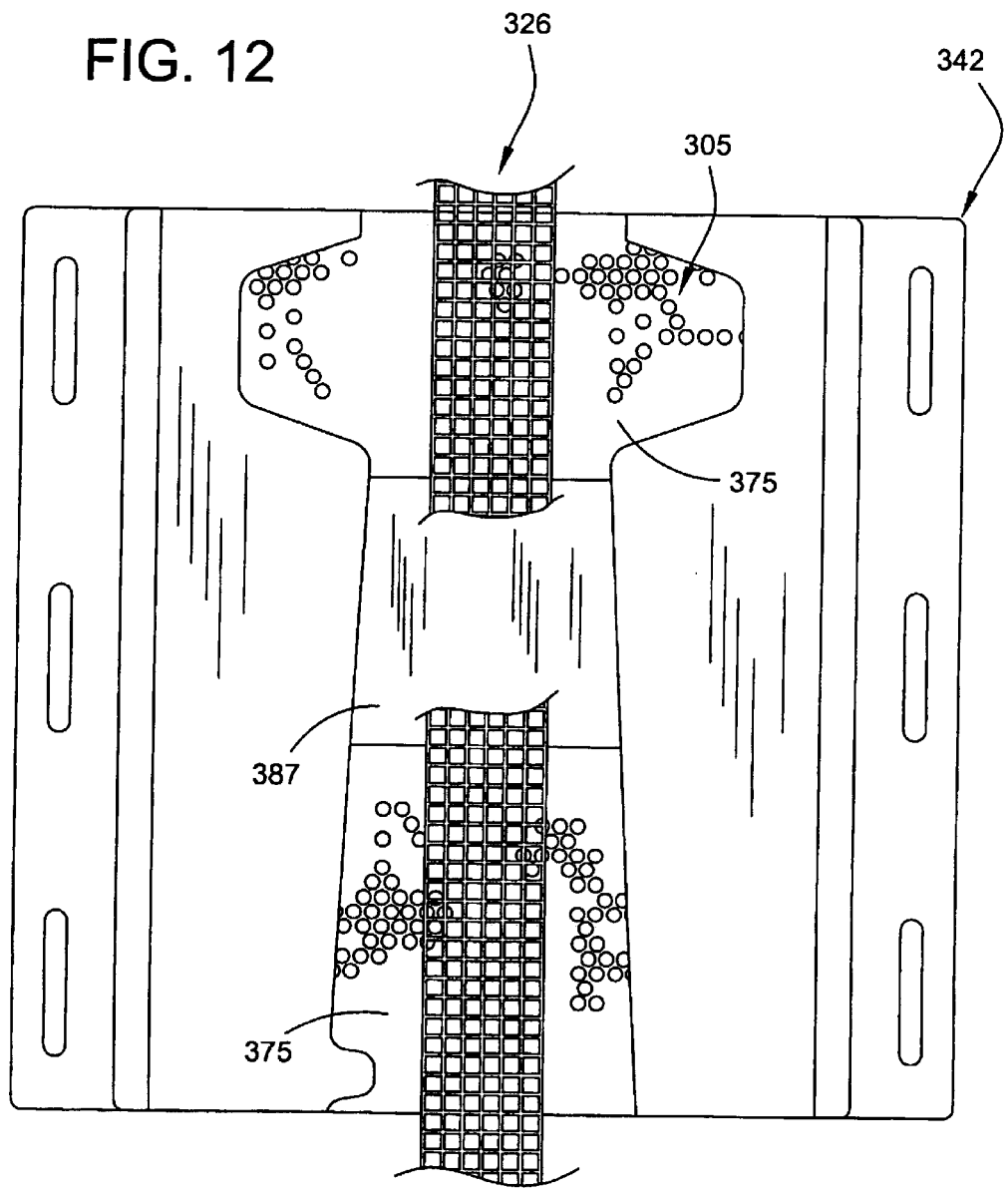
FIG. 12 is a top plan view of a form member of a fourth embodiment.
Figure 13:
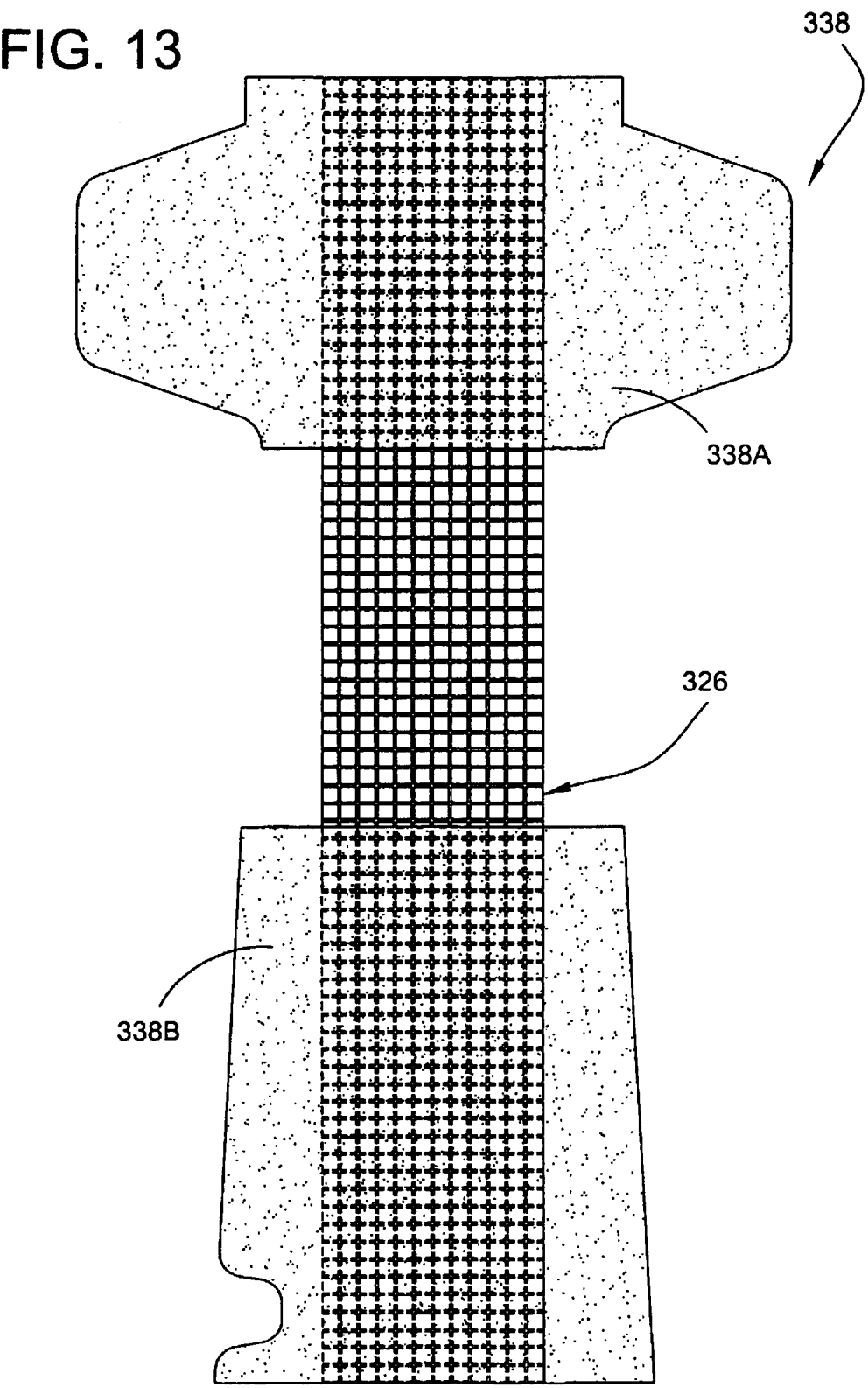
FIG. 13 is an absorbent core produced using the form member of FIG. 12.

A form member 342 of a fourth embodiment (shown in FIG. 12) may be used to make a ventilated absorbent core 338 (FIG. 13) having two longitudinally spaced sections 338A, 338B. Corresponding parts of the fourth embodiment of the form member 342 will be indicated by the same reference numerals as for the first embodiment of the form member 42, plus "300". The form member 342 has a central plateau 387 (broadly, "a support formation") which separates sections 375 of the forming surface 305. As with the central plateau 287 of the third embodiment, the plateau 387 is solid and does not draw fibers or other particles onto it during formation of the web (not shown) which is cut into the absorbent core 338. The central plateau 387 contacts and supports the scrim 326. Longitudinal end margins of the scrim 326 are embedded in each of the core sections 338A, 338B and connect the sections together. The scrim 326 unitizes these separate sections 338A, 338B, making it much easier to control the sections in manufacture and reducing the risk of tearing the sections.

Figure 14:
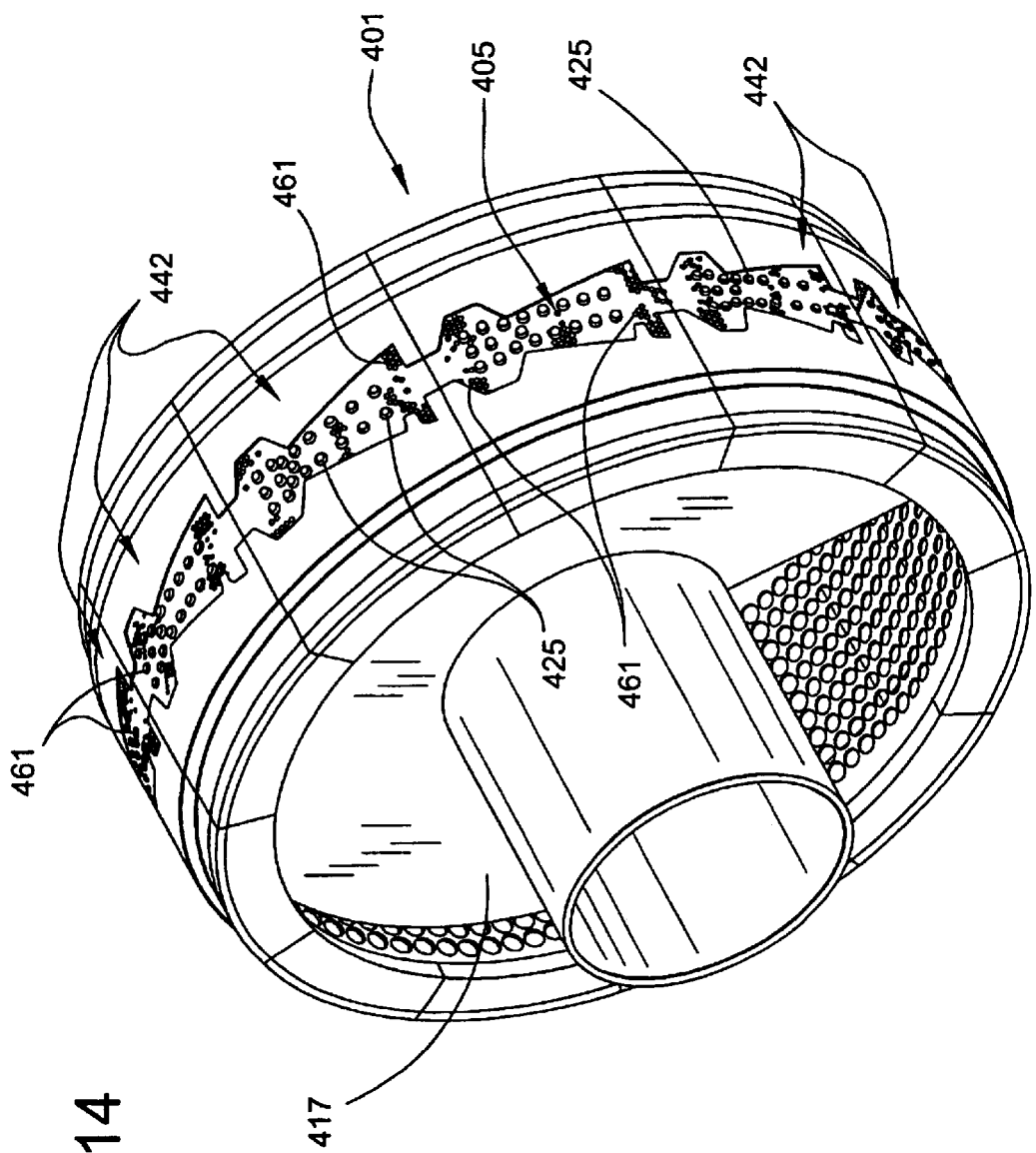
FIG. 14 is a schematic perspective of a forming drum having form members of a fifth embodiment.
Figure 15:
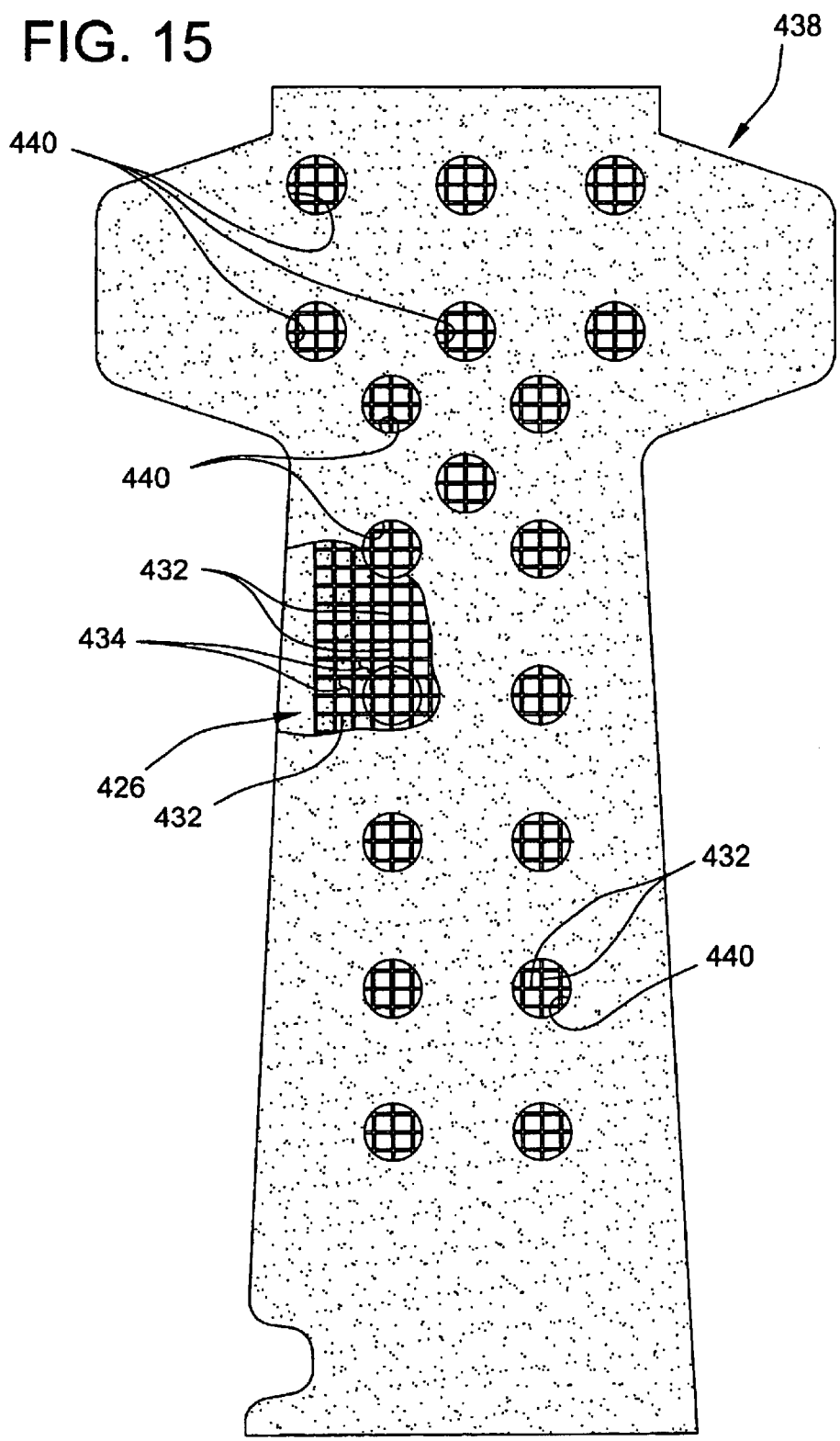
FIG. 15 is a top plan view of an absorbent core produced using the form member of FIG. 14.

Referring now to FIGS. 14 and 15, a forming drum 407 of air forming apparatus (not shown, but closely similar to the air forming apparatus of FIGS. 1 and 2) is shown for making a ventilated, reinforced absorbent core 438. Absorbent cores of this type are disclosed in patent application Ser. No. 10/306,185 field on Nov. 27, 2002, referenced above. In one form of the breathable absorbent core shown in FIG. 15, the core has multiple zones of higher air permeability which take the form of passages 440 extending fully through the absorbent core. However, one or more zones of higher air permeability may be formed otherwise than by passages 440 which extend through the absorbent core without departing from the scope of the present invention. The absorbent core 438 is reinforced with scrim 426, which may be seen in the passages of the absorbent core and where the core is broken away in FIG. 15.

The drum 407 includes a foraminous forming surface 405 located on the radially outward facing periphery of the drum. A vacuum duct 417 communicates vacuum pressure to the forming surface 405 for drawing fluidized fibers in an air forming chamber (not shown) onto the forming surface, as the forming surface rotates through the forming chamber, to build up a fibrous web (which is later cut into individual absorbent cores 438) having embedded scrim 426. The remainder of the air forming apparatus will not be described, being similar to that shown in FIGS. 1 and 2. Moreover, apparatus for forming absorbent cores may also be found in co-assigned U.S. patent application Ser. No. 10/306,269, entitled PROCESS AND APPARATUS FOR MAKING A REINFORCED FIBROUS ABSORBENT MEMBER by Venturino et al., filed on Nov. 27, 2002 simultaneously herewith. Another suitable apparatus is shown and described in co-assigned U.S. patent application Ser. No. 10/305,755 entitled PROCESS AND APPARATUS FOR AIR FORMING AN ARTICLE HAVING A PLURALITY OF REINFORCED SUPERIMPOSED FIBROUS LAYERS by Heyn et al., filed on Nov. 27, 2002 simultaneously herewith. The disclosures of these applications are incorporated herein by reference.

As may be seen in FIG. 14, the forming surface 405 is defined by a multiplicity of form members of a fifth embodiment, each designated generally at 442. Each form member 442 has a foraminous surface through which air readily passes, but on which fibers (and other material) in the forming chamber are deposited to form the fibrous web. Referring now also to FIGS. 16 and 17, each form member 442 includes perforated plate 461, allowing air to pass through, but capturing fibers on the forming surface 405. The perforated plate 461 includes nubs 425 projecting up from the plate. The nubs 425 are not porous so that fibers are generally not deposited on the nubs. Thus, the nubs 425 form the openings 440 in the absorbent core. Formation of openings in an absorbent core is known. An example of forming openings using nubs may be found in co-assigned U.S. Pat. No. 6,220,999, entitled METHOD AND APPARATUS FOR FORMING AN APERTURED PAD, by Kugler et al., which issued Apr. 24, 2001, the disclosure of which is incorporated herein by reference.

To form the absorbent core 438 of FIG. 15, the scrim 426 is guided from a roll 428 so that junctions where strands 432 of the scrim intersect each other rest on top of the nubs 425. Scrim 426 having a smaller mesh size (i.e., smaller than the diameter of the nubs 425 at their upper ends) is used. The smaller mesh size helps to assure that the nubs 425 will not be received in the openings 434 of the scrim 426 so that the scrim will rest on top of the nubs. The placement of scrim 426 onto a forming surface 405 in this manner is illustrated schematically in FIG. 18. It is to be understood that the junctions may rest anywhere on the nubs 425, not necessarily in the center, as shown.

Figure 18:
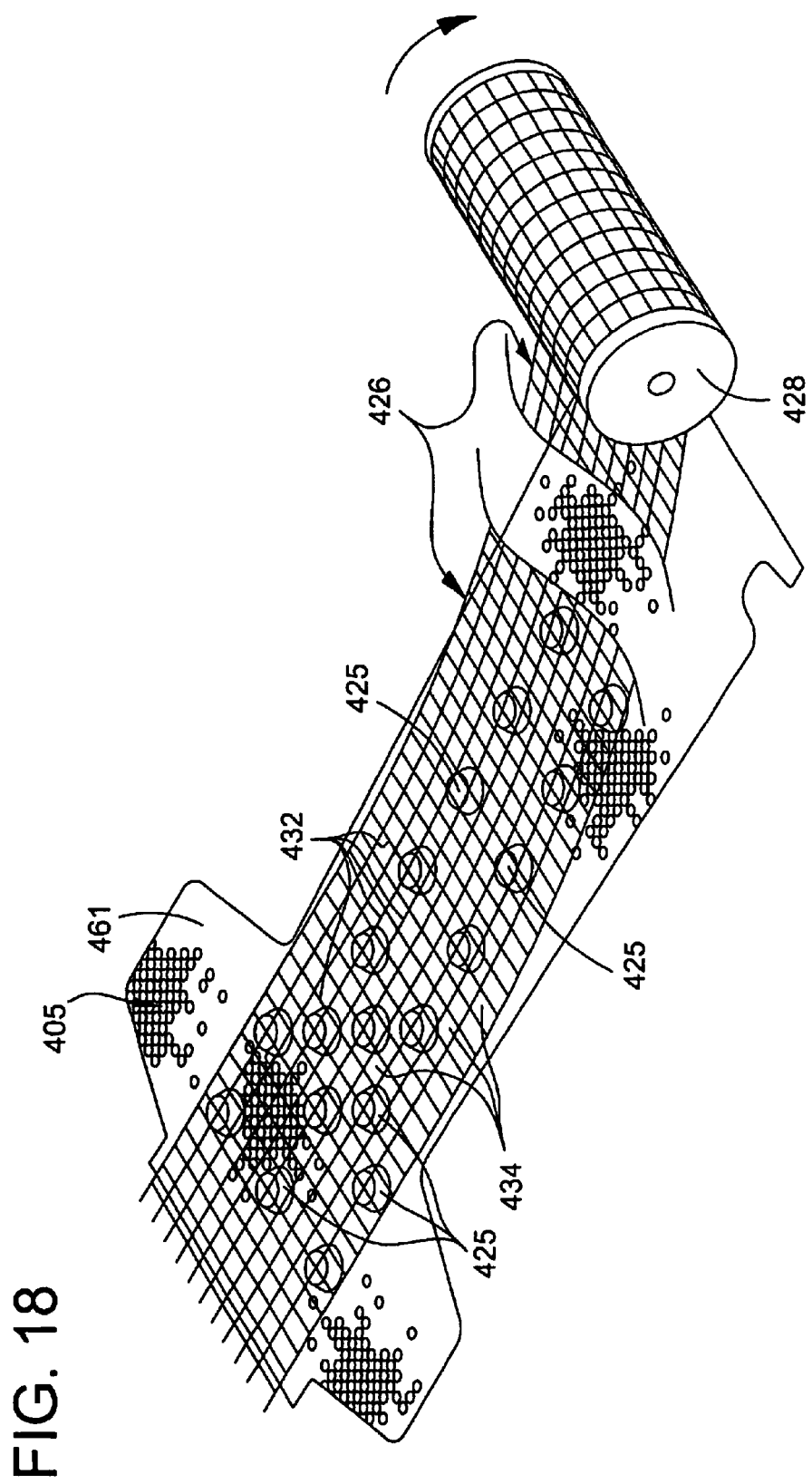
FIG. 18 is a schematic, fragmentary section of the form member illustrating the form member of FIG. 16 receiving the reinforcing scrim on top of nubs in the form member.
Figure 19:
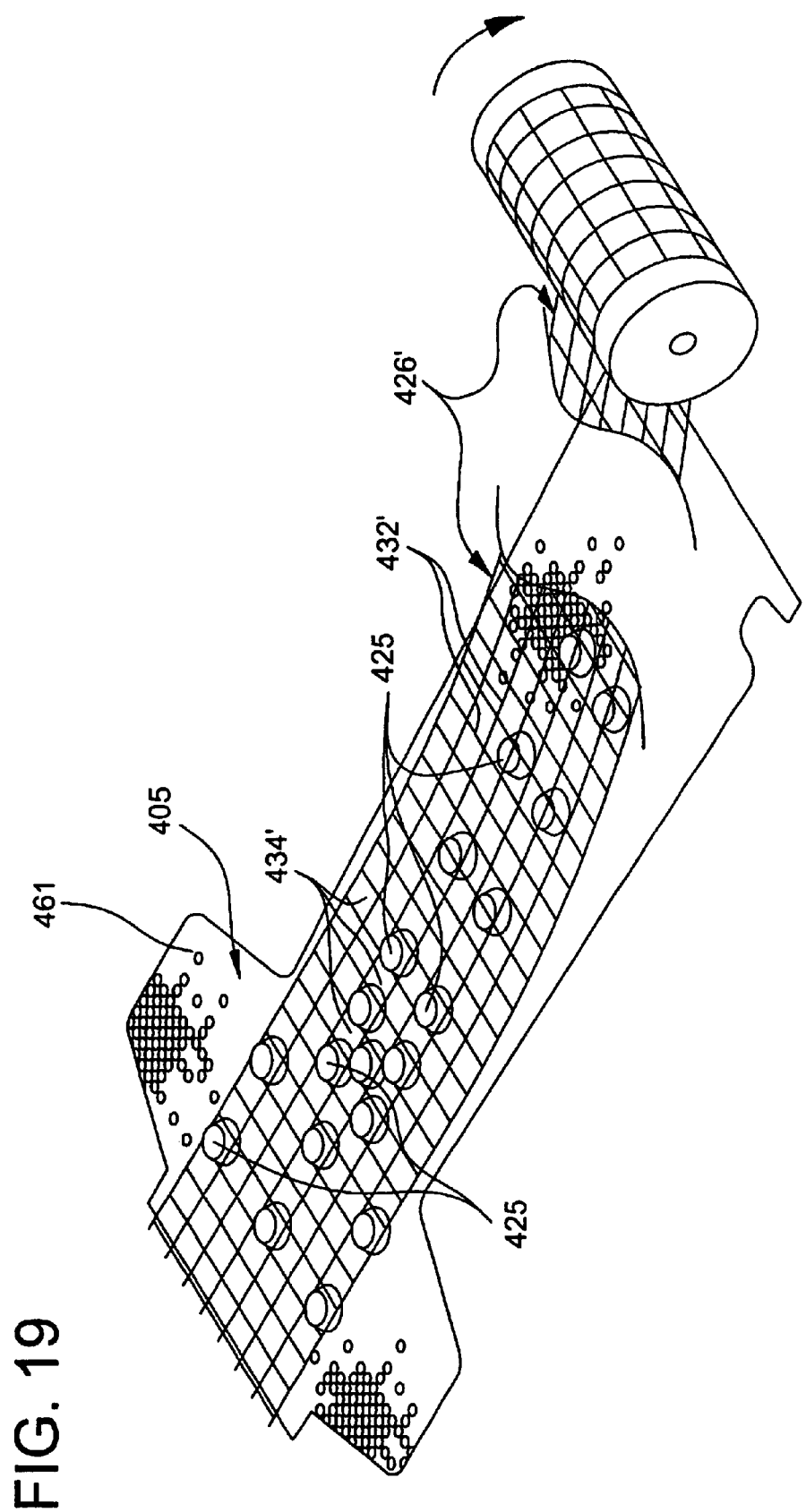
FIG. 19 is a schematic, fragmentary section of the form member of FIG. 16 illustrating the form member receiving the reinforcing scrim so that nubs of the form member are received in openings of the scrim.

The nubs 425 can be beneficially used to locate the scrim in the thickness or z-direction ZD of the core. The scrim may rest on top of the nubs 425 as shown in FIG. 18, or scrim 426 may fit part way down on the nubs. The placement of scrim 426' onto the forming surface 405 so that the nubs 425 are received into openings 434' of scrim is shown in FIG. 19. An absorbent core (not shown) manufactured according to FIG. 19 would have openings which are in registration with the scrim openings 434' so that the scrim 426' would not appear in the openings of the absorbent core, as does the scrim 426 of the absorbent core 438 shown in FIG. 15. Whether the scrim rests on top of the nubs 425 or is received down onto the nubs, the z position of the scrim is established by the nubs. It will be appreciated that by changing the height and/or diameter of the nubs 425, the position of the scrim 426, 426' within the absorbent core may be changed. In some circumstances it may be desirable to have nubs (not shown) of different height on the same screen. For example if a forming surface has a pocket, nubs to support the reinforcing member in the pocket might be taller than nubs to support the reinforcing member outside the pocket.

Figure 20A:
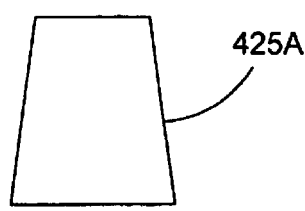
FIGS. 20A–20F are schematic illustrations of forming nubs for form members.
Figure 20B:
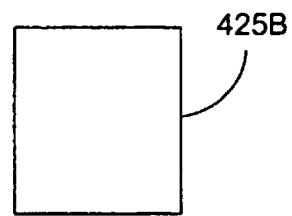
Figure 20C:
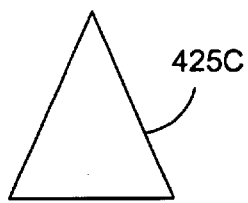
Figure 20D:
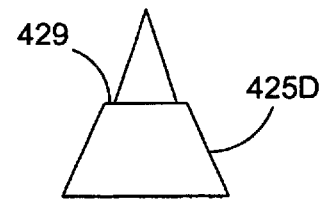
Figure 20E:
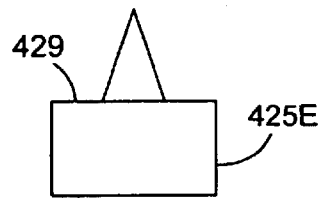

The nubs may have different configurations, some of which are illustrated in FIGS. 20A–20F. In FIG. 20A, the nub 425A may be sized slightly larger than the scrim opening 434' so that the nub is received in the scrim opening through deformation of the scrim, and an interference fit holds the scrim in position above the bottom of the nub and above the perforated plate 461. FIGS. 20A and 20C show nubs 425A, 425C which taper smoothly toward their free ends to facilitate starting the scrim opening 434 on the nubs. The tapered nubs 425A, 425C also promote release of the fibrous web from the forming surface 405 by providing a release angle. The scrim 426' also provides a continuous peel force to remove the formed fibrous web from the forming surface 405. The scrim 426' moves down on the nub 425A, 425C until the nub diameter is the same or slightly larger than the opening of the scrim. Tapered nubs 425D, 425E of FIGS. 20D and 20E are similar, but have shoulders 429 which contact and positively locate the scrim at a fixed height. By manipulation of the height and width of the nubs 425D, 425E (and locations of the shoulders 429) the location of the scrim in the thickness or z-direction ZD can be selected. It is also envisioned that by making the nubs 425 sufficiently short, the openings would not extend completely through the absorbent core, leaving rather instead dimples (not shown) in one face of the absorbent core.

Figure 20F:
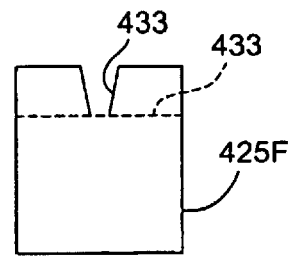

Although the nubs 425A–425F illustrated are generally symmetrical, the nubs may have other, symmetrical and nonsymmetrical shapes. To form the absorbent core shown in FIG. 15, where the junction of intersecting strands of the scrim are located in the openings of the core, the scrim 426 is located in the forming chamber on top of the nubs. The nub 425F of FIG. 20F is formed with a pair of crossing, flared grooves 433 in its top surface for receiving strands 432 of the scrim 426 (not shown in FIG. 20F) at a junction to more positively locate the strands on the top of the nub. The flaring of the grooves 433 facilitates capturing and centering the strands on the nub. However, where scrim openings 434 are small (e.g., as in FIG. 18), the grooves 433 are not needed. Moreover, it is not necessary in that event to precisely control the placement of the scrim 426 as it is being placed onto the forming surface 405.

Figure 21A:
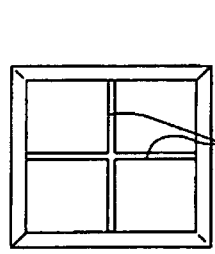
FIGS. 21A–21D are top plan views of nubs having scrim locating grooves.
Figure 21B:
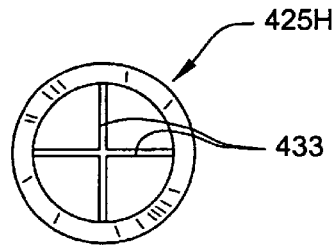
Figure 21C:
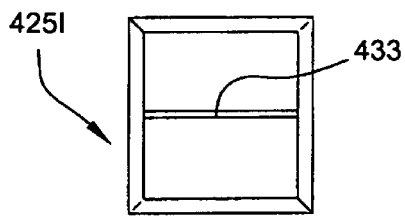
Figure 21D:
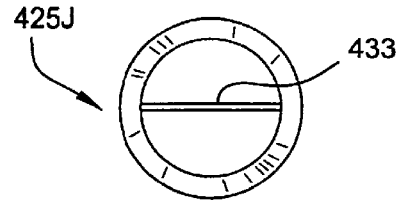
Figure 22A:
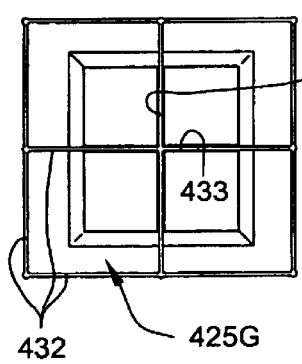
FIGS. 22A–22C are schematic top plan views of nubs having grooves and scrim being located in the grooves.
Figure 22B:
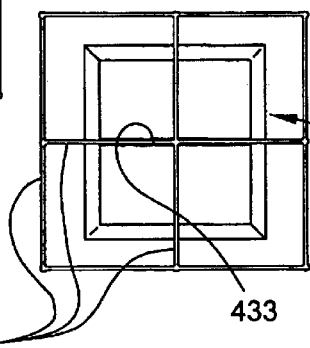
Figure 22C:
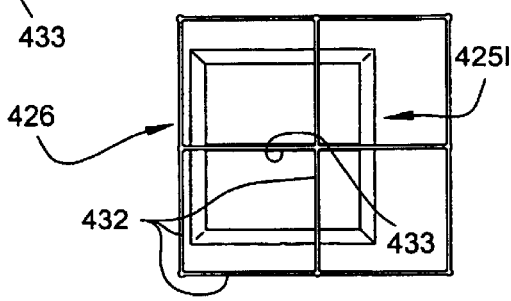

Other exemplary forms of grooved nubs are shown in FIGS. 21A–21D. FIGS. 21A and 21B show nubs 425G, 425H which have two, intersecting grooves 433 like the nub 425F of FIG. 20F. However, the nubs 425G, 425H of FIGS. 21A and 21B are tapered. Receipt of a section of scrim 426 onto the nub 425G is schematically illustrated in FIG. 22A. It may be seen how the intersecting grooves 433 receive and locate the scrim relative to the nub 425G. Nubs 425I, 425J, having but a single groove 433, are shown in FIGS. 21C and 21D. It is believed not necessary to have two grooves to locate the scrim. Moreover, location in two directions is not believed to be necessary. FIGS. 22B and 22C illustrate scrim 426 having a single strand 432 received in the groove 433 of the nub 425I, in two different positions relative to the nub. Other constructions for capturing the scrim on the nubs may be used without departing from the scope of the present invention. As discussed above, it is not believed to be necessary for the nubs capture the scrim or to locate the scrim in any way to achieve the goals of the present invention. However, it may be desirable to achieve such location of the scrim, such as for zoned placement of the scrim within the absorbent core.

Figure 23:
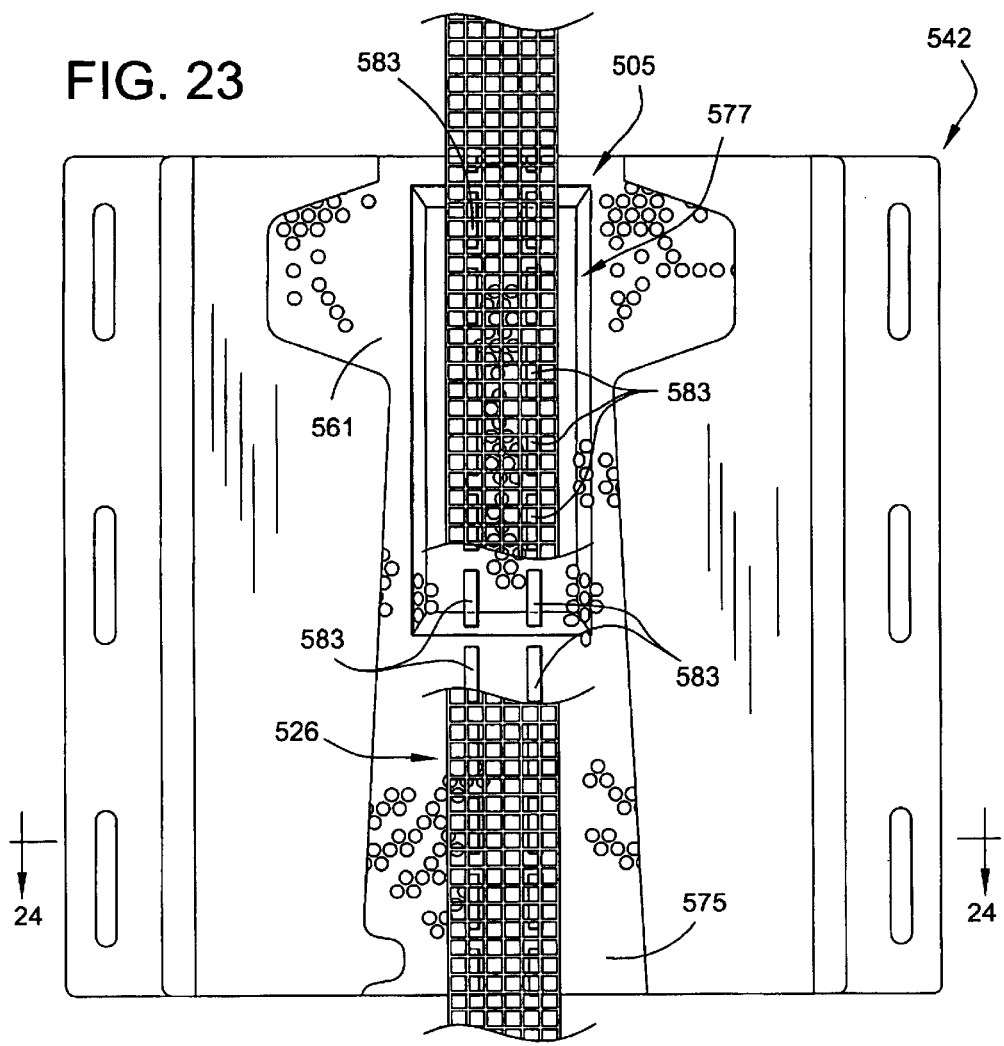
FIG. 23 is a top plan view of a form member of a sixth embodiment.
Figure 24:
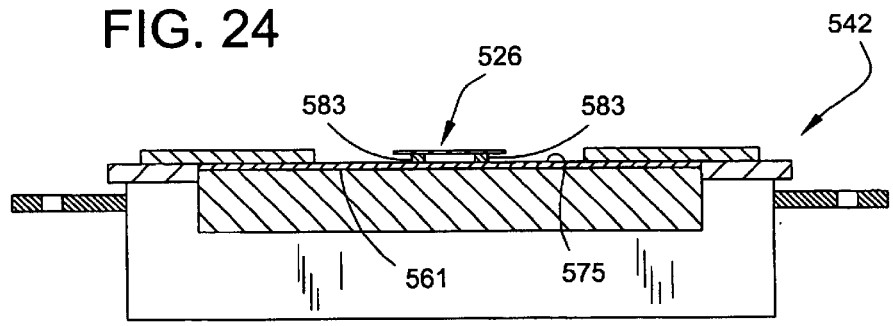
FIG. 24 is a section taken in the plane including line 24—24 of FIG. 23.

Referring now to FIGS. 23 and 24, a form member 542 of a sixth embodiment is shown to include a forming surface 505 defined on a perforated plate 561. The forming surface 505 further includes a pocket 577 defined by the perforated plate 561. In the sixth embodiment, the support formation for supporting the reinforcing member (i.e., scrim 526) above the lowermost part of the forming surface 505 is formed by support rails 583. The support rails 583 are solid, not having openings which permit the passage of air through the rails. Moreover, the rails 583 are not, in the illustrated embodiment, formed by the perforated plate 561. Each rail is illustrated as being discontinuous along its length (i.e., including multiple aligned, longitudinally separated segments), but may be continuous without departing from the scope of the present invention.

It will be readily apparent that various conventional devices and techniques can be employed to further process the web 3. For example, the web can be debulked at a debulking station (not shown). It is believed that debulking enhances fiber entanglement with the scrim (26, 126, etc.) so that a stronger interconnection of the scrim and fibrous material F may be achieved. In addition, various conventional devices and techniques (not shown) can be employed to sever fibrous web 3 into predetermined lengths to provide selected air formed fibrous articles. The severing system may, for example, include a die cutter, a water cutter, rotary knives, reciprocating knives, energy beam cutters, particle beam cutters or the like, as well as combinations thereof. After severing, the discrete fibrous pads can be transported and delivered for further processing operations, as desired.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A form for use in making an air formed, reinforced fibrous web, the form comprising a foraminous surface having a length and a width and adapted to collect fluent fibrous material driven by fluid pressure toward the foraminous surface to form the fibrous web, the foraminous surface being formed to contact and support a reinforcing member at a location selected for positioning the reinforcing member within the thickness of the fibrous web.

2. A form as set forth in claim 1 wherein the foraminous surface includes a bottom surface having a lowermost portion, the foraminous surface positioning the reinforcing member above the lowermost portion of the bottom surface.

3. A form as set forth in claim 2 wherein the foraminous surface includes a first section located generally higher than the bottom surface, the foraminous surface being shaped and arranged to position at least a portion of the reinforcing member at a location lower than the first section.

4. A form as set forth in claim 1 wherein the foraminous surface defines at least one support formation extending continuously over the foraminous surface.

5. A form as set forth in claim 4 wherein said at least one support formation extends continuously lengthwise direction of the foraminous surface.

6. A form as set forth in claim 4 wherein said at least one support formation extends continuously widthwise of the foraminous surface.

7. A form as set forth in claim 1 wherein the foraminous surface defines at least one support formation, the support formation being discontinuous over the foraminous surface.

8. A form as set forth in claim 1 wherein the foraminous surface is shaped to contact the reinforcing member at least at two spaced apart locations.

9. A form as set forth in claim 8 wherein the foraminous surface is substantially non-linear in transverse cross section.

10. A form as set forth in claim 8 wherein foraminous surface is formed with at least two, spaced apart ridges disposed for contacting and supporting the reinforcing member.

11. A form as set forth in claim 10 wherein the ridges are formed by bends in the foraminous surface.

12. A form as set forth in claim 10 wherein the ridges are everywhere perforated to permit passage of fluid therethrough.

13. A form as set forth in claim 10 wherein the ridges extend continuously over the foraminous surface.

14. A form as set forth in claim 13 wherein the ridges extend lengthwise the entire length of the form.

15. A form as set forth in claim 10 wherein at least one of the ridges is discontinuous over the foraminous surface.

16. A form as set forth in claim 1 wherein the foraminous surface is stepped in transverse cross section, at least one of the steps being sized and positioned for contacting and supporting a reinforcing member.

17. A form as set forth in claim 16 wherein the foraminous surface includes at least two, spaced apart steps arranged for contacting and supporting the reinforcing member generally between the steps.

18. A form as set forth in claim 16 wherein at least two of the steps are arranged for contact with longitudinal edge margins of the reinforcing member for locating reinforcing member widthwise of the foraminous surface.

19. A form as set forth in claim 1 wherein the foraminous surface is formed for contacting the reinforcing member to locate the reinforcing member widthwise of the foraminous surface.

20. A form as set forth in claim 1 wherein the foraminous surface includes a support formation sized and arranged for contacting and supporting the reinforcing member, said support formation being substantially free of openings for use in drawing fibrous material onto said support formation.

21. A form as set forth in claim 20 wherein the foraminous surface further includes sections disposed on opposite sides of said support formation, the sections having openings for use in drawing fibrous material onto the sections.

22. A form as set forth in claim 21 wherein said support formation extends lengthwise of the foraminous surface and said sections are located on laterally opposite sides of said support formation.

23. A form as set forth in claim 22 wherein the foraminous surface includes channels on laterally opposite sides of said support formation.

24. A form as set forth in claim 21 wherein said support formation extends transversely of the foraminous surface and said sections are located on longitudinally opposite sides of said support formation.

25. A form as set forth in claim 1 wherein the foraminous surface includes support formations in the form of nubs projecting outwardly from the foraminous surface, the nubs being sized and arranged for contacting and supporting the reinforcing member.

26. A form as set forth in claim 25 wherein the nubs are free of openings for use in drawing fibrous material onto the nubs.

27. A form as set forth in claim 26 wherein at least some of the nubs have at least one groove therein for use in capturing the reinforcing member to locate it relative to the foraminous surface.

28. A form as set forth in claim 1 in combination with other forms of the same construction arranged in a cylinder on a rotatable drum.

29. A form as set forth in claim 1 further comprising at least one support formation for contacting and supporting the reinforcing member, said at least one support formation being surrounded by at least one section of the foraminous surface which does not support the reinforcing member.

30. A form as set forth in claim 1 further comprising at least one support formation in the form of at least one rail on the foraminous surface, the rail being nonporous.

31. Apparatus for forming a reinforced fibrous web comprising a form, a reinforcing member delivery system for delivering a reinforcing member to the form, a forming chamber adapted to deliver fluent fibrous material generally to the form, a vacuum source for applying a vacuum to draw the fluent material onto the form, the form comprising a foraminous surface having a length and a width and being adapted to collect fluent fibrous material driven by fluid pressure toward the foraminous surface to form the fibrous web, the foraminous surface being formed to contact and support the reinforcing member at a location selected for positioning the reinforcing member within the thickness of the fibrous web.

32. Apparatus as set forth in claim 31 wherein the forming chamber has an entrance and an exit, the form being movable along a path from the entrance to the exit having a length, the delivery system being positioned relative to the forming chamber for feeding the reinforcing member onto the foraminous surface at locations from prior to entering the forming chamber to locations in the forming chamber no greater than about 25% of the length of the path from the entrance along the path.

33. Apparatus as set forth in claim 32 wherein the delivery system is positioned relative to the forming chamber for feeding the reinforcing member onto the foraminous surface at locations from prior to entering the forming chamber to locations in the forming chamber no greater than about 15% of the length of the path from the entrance along the path.

34. Apparatus as set forth in claim 33 wherein the delivery system is arranged to deliver the reinforcing member onto the form prior to entry of the form into the forming chamber.

35. Apparatus as set forth in claim 31 wherein the foraminous surface includes a bottom surface having a lowermost portion, the foraminous surface positioning the reinforcing member above the lowermost portion of the bottom surface.

36. Apparatus as set forth in claim 31 wherein the foraminous surface includes a first section located generally higher than the bottom surface, the foraminous surface being shaped and arranged to position at least a portion of the reinforcing member at a location lower than the first section.

37. Apparatus as set forth in claim 31 wherein the foraminous surface defines at least one support formation extending continuously over the foraminous surface.

38. Apparatus as set forth in claim 37 wherein said at least one support formation extends continuously lengthwise direction of the foraminous surface.

39. Apparatus as set forth in claim 37 wherein said at least one support formation extends continuously widthwise of the foraminous surface.

40. Apparatus as set forth in claim 31 wherein the foraminous surface defines at least one support formation, the support formation being discontinuous over the foraminous surface.

41. Apparatus as set forth in claim 31 wherein the foraminous surface is shaped to contact the reinforcing member at least at two spaced apart locations.

42. Apparatus as set forth in claim 31 wherein the foraminous surface is substantially non-linear in transverse cross section.

43. Apparatus as set forth in claim 31 wherein foraminous surface is formed with at least two, spaced apart ridges disposed for contacting and supporting the reinforcing member.

44. Apparatus as set forth in claim 43 wherein the ridges are formed by bends in the foraminous surface.

45. Apparatus as set forth in claim 43 wherein the ridges are everywhere perforated to permit passage of fluid therethrough.

46. Apparatus as set forth in claim 43 wherein the ridges extend continuously over the foraminous surface.

47. Apparatus as set forth in claim 46 wherein the ridges extend lengthwise the entire length of the form.

48. Apparatus as set forth in claim 43 wherein at least one of the ridges is discontinuous over the foraminous surface.

49. Apparatus as set forth in claim 31 wherein the foraminous surface is stepped in transverse cross section, at least one of the steps being sized and positioned for contacting and supporting a reinforcing member.

50. Apparatus as set forth in claim 49 wherein the foraminous surface includes at least two, spaced apart steps arranged for contacting and supporting the reinforcing member generally between the steps.

51. Apparatus as set forth in claim 49 wherein at least two of the steps are arranged for contact with longitudinal edge margins of the reinforcing member for locating reinforcing member widthwise of the foraminous surface.

52. Apparatus as set forth in claim 31 wherein the foraminous surface is formed for contacting the reinforcing member to locate the reinforcing member widthwise of the foraminous surface.

53. Apparatus as set forth in claim 31 wherein the foraminous surface includes a support formation sized and arranged for contacting and supporting the reinforcing member, said support formation being substantially free of openings for use in drawing fibrous material onto support formation.

54. Apparatus as set forth in claim 53 wherein the foraminous surface further includes sections disposed on opposite sides of said support formation, the sections having openings for use in drawing fibrous material onto the sections.

55. Apparatus as set forth in claim 54 wherein said support formation extends lengthwise of the foraminous surface and said sections are located on laterally opposite sides of said support formation.

56. Apparatus as set forth in claim 55 wherein the foraminous surface includes channels on laterally opposite sides of support formation.

57. Apparatus as set forth in claim 56 wherein said support formation extends transversely of the foraminous surface and said sections are located on longitudinally opposite sides of said support formation.

58. Apparatus as set forth in claim 31 wherein the foraminous surface includes nubs projecting outwardly from the foraminous surface, the nubs being sized and arranged for contacting and supporting the reinforcing member.

59. Apparatus as set forth in claim 58 wherein the nubs are free of openings for use in drawing fibrous material onto the nubs.

60. Apparatus as set forth in claim 59 wherein at least some of the nubs have at least one groove therein for use in capturing the reinforcing member to locate it relative to the foraminous surface.

61. Apparatus as set forth in claim 31 further comprising a conveyor for receiving the fibrous web from the form to convey the fibrous web away from the form.

62. Apparatus as set forth in claim 61 further comprising a vacuum device for removing the fibrous web from the form.

63. Apparatus as set forth in claim 31 wherein the form comprises a series of form members.

64. Apparatus as set forth in claim 63 further comprising a drum mounted for rotation about an axis, the form members being disposed around the circumference of the drum.

65. Apparatus as set forth in claim 31 further comprising a scarfing device for shaping the formed fibrous web.

66. Apparatus as set forth in claim 31 further comprising at least one support formation for contacting and supporting the reinforcing member, said at least one support formation being surrounded by a section of the foraminous surface which does not support the reinforcing member.

67. Apparatus as set forth in claim 31 further comprising at least one support formation in the form of at least one rail on the foraminous surface, the rail being nonporous.

68. A method for forming a reinforced fibrous web for use in the manufacture of absorbent articles, the method comprising:

moving a forming surface through a forming chamber;

delivering a reinforcing member into contact with the moving forming surface so that the reinforcing member is positioned relative to the forming surface by contact therewith;

delivering fibrous material in the forming chamber to the forming surface, such that at least some of the fibrous material passes through the reinforcing member and is deposited on the forming surface, and at least some of the fibrous material is entangled with the reinforcing member to form the fibrous web.

69. A method as set forth in claim 68 wherein said step of delivering a reinforcing member into contact with the forming surface occurs prior to said step of delivering fibrous material to the forming surface.

70. A method as set forth in claim 68 further comprising selecting a forming surface formed with support formations sized and arranged for contacting and supporting the reinforcing member at a position corresponding to a predetermined position of the reinforcing member within the thickness of the fibrous web.

71. A method as set forth in claim 70 further comprising replacing the support formations to change the position of the reinforcing member within the thickness of the fibrous web.

* * * * *